US012751999B2

(12) United States Patent
Bevers et al.

(10) Patent No.: US 12,751,999 B2
(45) Date of Patent: Oct. 6, 2026

(54) LIPID NANOPARTICLES COMPRISING STEROLS AND mRNA

(71) Applicants: ETHERNA IMMUNOTHERAPIES NV, Niel (BE); Vrije Universiteit Brussel, Brussels (BE)

(72) Inventors: Sanne Bevers, Niel (BE); Stefaan De Koker, Niel (BE); Raymond Michel Schiffelers, Yalelaan (NL); Sander Alexander Antonius Kooijmans, Yalelaan (NL)

(73) Assignees: eTheRNA Immunitherapies NV, Niel (BE); Vrije Universiteit Brussel, Brussels (BE)

(*) Notice: Subject to any disclaimer, the term of this patent is extended or adjusted under 35 U.S.C. 154(b) by 925 days.

(21) Appl. No.: 18/008,877

(22) PCT Filed: Jun. 11, 2021

(86) PCT No.: PCT/EP2021/065856
§ 371 (c)(1),
(2) Date: Dec. 7, 2022

(87) PCT Pub. No.: WO2021/250263
PCT Pub. Date: Dec. 16, 2021

(65) Prior Publication Data

US 2024/0261381 A1 Aug. 8, 2024

(30) Foreign Application Priority Data

Jun. 11, 2020 (EP) .................................... 20179435
Mar. 3, 2021 (EP) .................................... 21160384

(51) Int. Cl.

| | |
|---|---|
| ***A61K 39/00*** | (2006.01) |
| ***A61K 9/51*** | (2006.01) |
| ***A61K 47/24*** | (2006.01) |
| ***A61K 47/28*** | (2006.01) |
| ***A61P 35/00*** | (2006.01) |
| ***A61P 37/04*** | (2006.01) |

(52) U.S. Cl.
CPC .... *A61K 39/001117* (2018.08); *A61K 9/5123* (2013.01); *A61K 9/5146* (2013.01); *A61K 39/0011* (2013.01); *A61K 39/001102* (2018.08); *A61K 47/24* (2013.01); *A61K 47/28* (2013.01); *A61P 35/00* (2018.01); *A61P 37/04* (2018.01); *A61K 2039/53* (2013.01); *A61K 2039/575* (2013.01)

(58) Field of Classification Search
CPC ........ A61K 39/001117; A61K 2039/53; A61P 37/04
See application file for complete search history.

(56) References Cited

U.S. PATENT DOCUMENTS

2015/0110857 A1 4/2015 Derosa et al.

FOREIGN PATENT DOCUMENTS

| | | | |
|---|---|---|---|
| JP | 2021511376 | A | 6/2021 |
| WO | 2012170889 | A1 | 12/2012 |
| WO | 2015071295 | A1 | 5/2015 |
| WO | 2016118725 | A1 | 7/2016 |
| WO | 2019141814 | A1 | 7/2019 |

OTHER PUBLICATIONS https://en.wikipedia.org/wiki/List_of_cancer_types—accessed May 22, 2020. (Year: 2020).*
https://www.cancer.gov/about-cancer/understanding/what-is-cancer—accessed May 22, 2020. (Year: 2020).*
International Search Report and Written Opinion mailed Jul. 6, 2021, reference to co-pending application No. PCT/EP2021/065856 filed Jun. 11, 2021.
European Search Report in reference to co-pending European Application No. 20179435, filed Jun. 11, 2020.
International Search Report and Written Opinion mailed Jul. 23, 2021, reference to co-pending application No. PCT/EP2021/065856 filed Jun. 11, 2021.
Reichmuth et al., mRNA vaccine delivery using lipid nanoparticles. Therapeutic Delivery. (2016) 7(5), 319-334.

* cited by examiner

*Primary Examiner* — Elly-Gerald Stoica
(74) *Attorney, Agent, or Firm* — DINSMORE & SHOHL LLP

(57) ABSTRACT

The present invention relates to the field of lipid nanoparticles (LNP); more specifically comprising an ionizable lipid, a phospholipid, a sterol, a PEG lipid and one or more nucleic acids. The LNP's of the present invention are characterized in comprising less than about 1 mol % of a C14-PEG2000 lipid; as well as particular percentages of the other lipids. The present invention provides use of the LNP's for immunogenic delivery of nucleic acid molecules, specifically mRNA; thereby making them highly suitable for use in vaccines, such as for the treatment of cancer or infectious diseases. Finally, methods are provided for preparing such LNP's.

18 Claims, 10 Drawing Sheets

A

B

A

B

C.

D

E

F

G

A

B

C

D

Fig. 6D –cont.
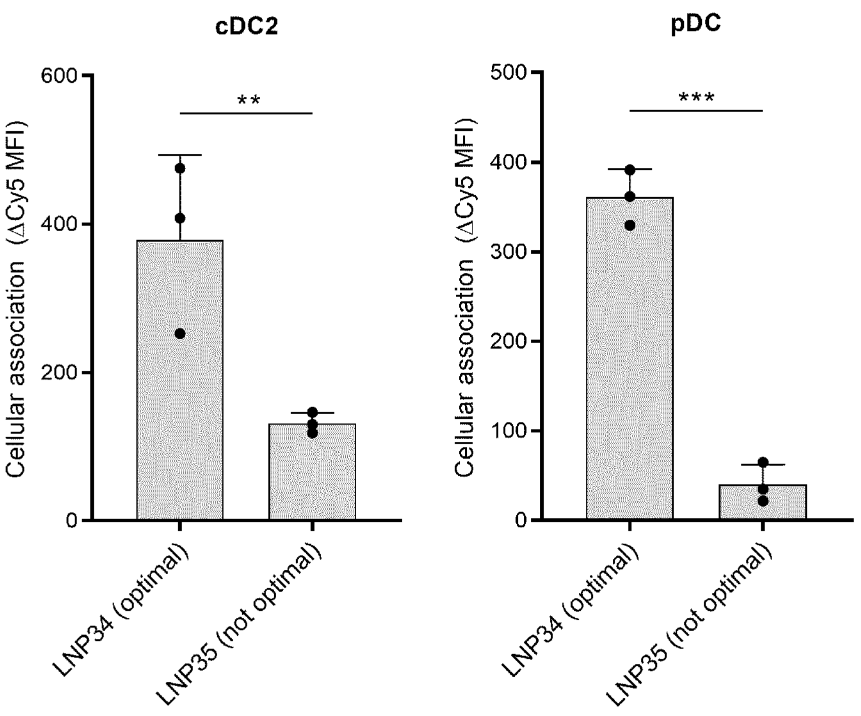
E
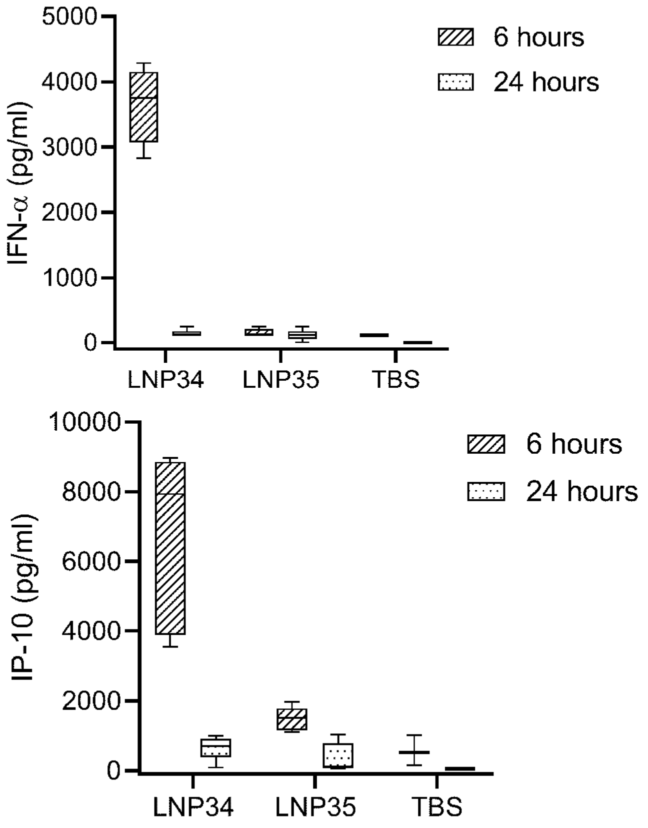

LIPID NANOPARTICLES COMPRISING STEROLS AND mRNA

CROSS REFERENCES TO RELATED APPLICATIONS

This application is a national-stage application under 35 U.S.C. § 371 of International Application No. PCT/EP2021/065856, filed Jun. 11, 2021, which International Application claims benefit of priority to European Patent Application No. 20179435.1, filed Jun. 11, 2020, and to European Patent Application No. 21160384.0, filed Mar. 3, 2021.

FIELD OF THE INVENTION

The present invention relates to the field of lipid nanoparticles (LNP); more specifically comprising an ionizable lipid, a phospholipid, a sterol, a PEG lipid and one or more nucleic acids. The LNP's of the present invention are characterized in comprising less than about 1 mol % of a C14-PEG2000 lipid; as well as particular percentages of the other lipids. The present invention provides use of the LNP's for immunogenic delivery of nucleic acid molecules, specifically mRNA; thereby making them highly suitable for use in vaccines, such as for the treatment of cancer or infectious diseases. Finally, methods are provided for preparing such LNP's.

BACKGROUND TO THE INVENTION

One of the major challenges in the field of targeted delivery of biologically active substances is often their instability and low cell penetrating potential. This is specifically the case for the delivery of nucleic acid molecules, in particular (m)RNA molecules. Therefore, proper packaging is crucial for adequate protection and delivery. Hence, there is a continuous need for methods and compositions for packaging biologically active substances, such as nucleic acids.

In that respect, lipid-based nanoparticle compositions such as lipoplexes and liposomes have been used as packaging vehicles for biologically active substances to allow transport into cells and/or intracellular compartments. These lipid-based nanoparticle compositions typically comprise a mixture of different lipids such as cationic lipids, ionizable lipids, phospholipids, structural lipids (such as sterols or cholesterol), PEG (polyethylene glycol) lipids, . . . (as reviewed in Reichmuth et al., 2016).

Lipid based nanoparticles composed of a mixture of 4 lipids—a cationic or ionizable lipid, a phospholipid, a sterol and a PEGylated lipid—have been developed for the non-immunogenic delivery of siRNA and mRNA to the liver after systemic administration. While many of such lipid compositions are known in the art, the ones used in mRNA delivery in vivo, typically comprise a level of PEG lipids of at least 1.5 mol, and have a low ratio of ionizable lipid:phospholipid, such as about 1:1-about 5:1.

We have now surprisingly found however, that the use of PEG lipids, at low amounts (i.e. less than about 1 mol %), give rise to nanoparticles which are highly suitable for immunogenic delivery of mRNA upon systemic injection of the LNP's. These effects were found to be even more pronounced by the combination of such low level PEG lipids with relatively high levels of ionizable lipid (i.e. between 55-70 mol %) and relatively low levels of phospholipids (i.e. less than about 10 mol %), accordingly for LNPs having relatively high ratio's of ionizable lipid:phospholipid (i.e. 6:1-11:1). In addition, some embodiments of the present invention feature low percentages of sterol (i.e. less than about 30 mol %, such as about 25 mol %).

SUMMARY OF THE INVENTION

In a first aspect, the present invention provides a lipid nanoparticle (LNP) comprising:

- an ionizable lipid;
- a phospholipid;
- a sterol;
- a PEG lipid; and
- one or more mRNA molecules;

characterized in that

- said PEG lipid is a C14-PEG lipid;
- said LNP comprises less than about 1 mol % of said PEG lipid;
- the molar percentage of said ionizable lipid is about and between 50-70 mol %; and
- the molar percentage of said sterol is about or above 25 mol %.

In a further aspect, the present invention provides a lipid nanoparticle (LNP) comprising:

- an ionizable lipid;
- a phospholipid;
- a sterol;
- a PEG lipid; and
- one or more mRNA molecules;

characterized in that

- said PEG lipid is a C14-PEG lipid;
- said LNP comprises less than about 1 mol % of said PEG lipid;
- the molar percentage of said ionizable lipid is about and between 50-60 mol %; and
- the molar percentage of said sterol is about or above 30 mol %.

In a further specific embodiment of the present invention, said LNP comprises about 0.5 mol %-about 0.9 mol % of said PEG lipid.

In another particular embodiment, the molar percentage of said phospholipid is less than about 10 mol %; preferably about 5 mol %.

In a further embodiment of the present invention, the ratio of ionizable lipid to phospholipid is above 5:1; preferably between about 6:1 and 11:1; most preferably about 11:1.

In yet a further embodiment of the present invention, the molar percentage of said ionizable lipid is about and between 55-60 mol %.

In a specific embodiment of the present invention, said C14-PEG lipid is a dimyristoyl lipid, i.e having 2 C14 fatty acid tails, such as said C14-PEG2000 lipid is preferably selected from the list comprising: a 1,2-Dimyristoyl-rac-glycero-3-methoxypolyethylene glycol-2000 (DMG-PEG2000). or 2-Dimyristoyl-sn-Glycero-3-Phosphoethanolamine glycol-2000 (DMPE-PEG2000).

In another particular embodiment of the present invention, said ionizable lipid is selected from the list comprising:

- 1,1-((2-(4-(2-((2-(bis(2-hydroxydodecyl)amino)ethyl)(2-hydroxydodecyl)amino)ethyl) piperazin-1-yl)ethyl) azanediyl)bis(dodecan-2-ol) (C12-200);

dilinoleylmethyl-4-dimethylaminobutyrate (DLin-MC3-DMA); or a compound of formula (I):

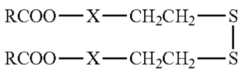

(I)

wherein:

RCOO is selected from the list comprising: myristoyl, α-D-Tocopherolsuccinoyl, linoleoyl and oleoyl; and X is selected from the list comprising:

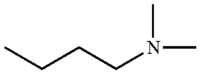

and

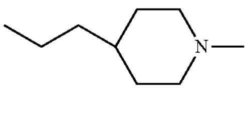

.

In a preferred embodiment, said ionizable lipid is a lipid of formula (I) wherein RCOO is α-D-Tocopherolsuccinoyl and X is

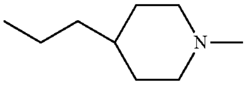

.

In yet a further embodiment of the present invention, said phospholipid is selected from the list comprising: 1,2-Dioleoyl-sn-glycero-3-phosphoethanolamine (DOPE), 1,2-Dioleoyl-sn-glycero-3-phosphocholine (DOPC), 1.2-distearoyl-sn-glycero-3-phosphocholine (DSPC) and mixtures thereof; in particular DOPE, DOPC and mixtures thereof.

In yet a further embodiment of the present invention, said sterol is selected from the list comprising cholesterol, ergosterol, campesterol, oxysterol, antrosterol, desmosterol, nicasterol, sitosterol and stigmasterol; preferably cholesterol.

In yet a further embodiment of the present invention, said LNP comprises between about 5-15 mol % of said phospholipid.

In a particular embodiment of the present invention, said LNP comprises:

about 50-70 mol % of said ionizable lipid;
about 5-15 mol % of said phospholipid;
about 0.5-0.9 mol % of said PEG lipid; and
balanced by the amount of said sterol.

In a particular embodiment of the present invention, said LNP comprises:

about 50-60 mol % of said ionizable lipid;
about 5-15 mol % of said phospholipid;
about 0.5-0.9 mol % of said PEG lipid; and
balanced by the amount of said sterol.

In a very specific embodiment of the present invention, said LNP comprises:

about 50 mol % of said ionizable lipid;
about 10 mol % of DOPE;
about 39.5 mol % of cholesterol; and
about 0.5 mol % of DMG-PEG2000.

In another very specific embodiment of the present invention, said LNP comprises:

about 56.5 mol % of said ionizable lipid;
about 5 mol % of DOPE;
about 38 mol % of cholesterol; and
about 0.5 mol % of DMG-PEG2000.

In another very specific embodiment of the present invention, said LNP comprises:

about 65 mol % of said ionizable lipid;
about 9.5 mol % of DOPE;
about 25 mol % of cholesterol; and
about 0.5 mol % of DMG-PEG2000.

In a more specific embodiment, said one or more mRNA molecules are selected from the list comprising immunomodulatory polypeptide-encoding mRNA and/or antigen-encoding mRNA. Said immunomodulatory-encoding mRNA may for example be selected from a list comprising mRNA molecules encoding for CD40L, CD70 and caTLR4.

In yet a further aspect, the present invention provides a pharmaceutical composition or a vaccine comprising one or more lipid nanoparticles as defined herein and an acceptable pharmaceutical carrier.

The present invention also provides the lipid nanoparticles, pharmaceutical compositions or vaccines as defined herein for use in human or veterinary medicine; in particular for use in the treatment of cancer or infectious diseases.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 6A. a. Luciferase activity in kidneys, lungs, heart, liver and spleen as % of total luciferase activity. FIG. 6B. Uptake of LNPs in multiple cell types as measured by difference in Cy5 MFI in LNP injected mice relative to TBS buffer injected mice FIG. 6C. Luciferase activity in kidneys, lungs, heart, liver and spleen as % of total luciferase activity. Optimal LNP34 showed increased luciferase activity in spleen compared with non-optimal LNPs (LNP35). FIG. 6D. Cellular uptake of optimal LNP34 is higher compared with non-optimal LNP35. FIG. 6E. Transient increases in IFN-α, and IP-10 cytokines in serum were observed (6 hours compared to 24 hours after LNP administration).

DETAILED DESCRIPTION OF THE INVENTION

Figure 1:
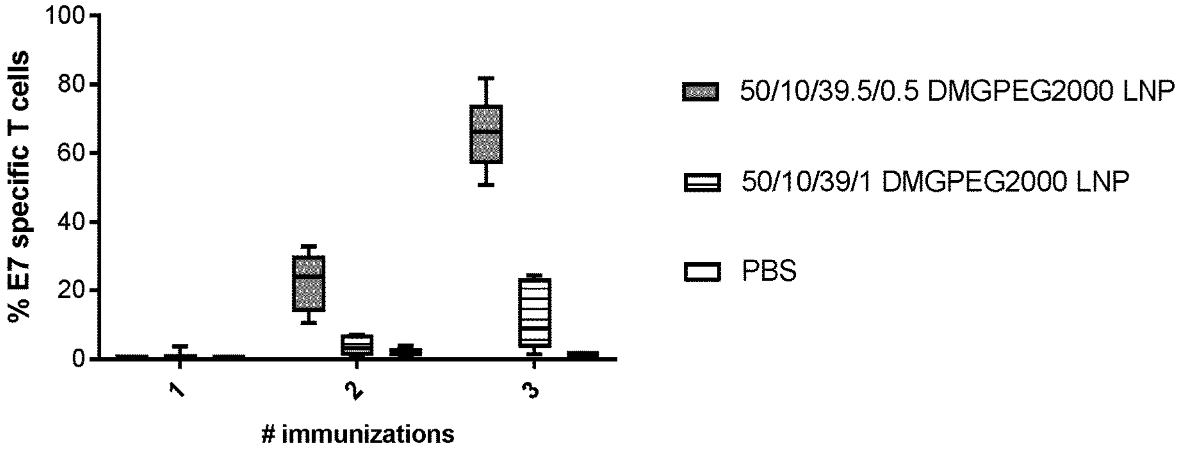
FIG. 1: Shows the results of three intravenous immunizations with E7 mRNA LNPs composed of SS-EC/DOPE/chol/DMG-PEG2000 at the indicated molar ratios.

As already detailed herein above, the present invention provides LNP's comprising C14-PEG lipids (e.g. C14-PEG2000 lipids), present at a relatively low amount (e.g. less than about 1 mol %), for which we have surprisingly found that these are highly suitable for immunogenic delivery of nucleic acids, specifically mRNA.

In the context of the present invention, "immunogenic delivery of nucleic acid molecules" means delivery of nucleic acid molecules to cells whereby contact with cells, internalization and/or expression inside the cells of said nucleic acids molecules results in induction of an immune response.

Therefore, in a first aspect, the present invention provides a lipid nanoparticle (LNP) comprising:

an ionizable lipid;
a phospholipid;
a sterol;
a PEG lipid; and
one or more mRNA molecules;

characterized in that said PEG lipid is a C14-PEG lipid;
said LNP comprises less than about 1 mol % of said PEG lipid;
the molar percentage of said ionizable lipid is about and between 50-70 mol %; and
the molar percentage of said sterol is about or above 25 mol %.

In a further embodiment, the present invention provides a lipid nanoparticle (LNP) comprising:

an ionizable lipid;
a phospholipid;
a sterol;
a PEG lipid; and
one or more nucleic acid molecules; in particular mRNA molecules;

characterized in that said PEG lipid is a C14-PEG lipid;
said LNP comprises less than about 1 mol % of said PEG lipid;
the molar percentage of said ionizable lipid is about and between 50-60 mol %; and
the molar percentage of said sterol is about or above 30 mol %.

In a further specific embodiment of the present invention, said LNP comprises about 0.5 mol %-about 0.9 mol % of said PEG lipid.

A lipid nanoparticle (LNP) is generally known as a nanosized particle composed of a combination of different lipids. While many different types of lipids may be included in such LNP, the LNP's of the present invention are typically composed of a combination of an ionizable lipid, a phospholipid, a sterol and a PEG lipid.

As used herein, the term "nanoparticle" refers to any particle having a diameter making the particle suitable for systemic, in particular intravenous administration, of, in particular, nucleic acids, typically having a diameter of less than 1000 nanometers (nm), preferably less than 500 nm, even more preferably less than 200 nm, such as for example between 50 and 200 nm; preferably between 80 and 160 nm.

In the context of the present invention, the term "PEG lipid" or alternatively "PEGylated lipid" is meant to be any suitable lipid modified with a PEG (polyethylene glycol) group. The PEG lipids of the present invention are characterized in being C14-PEG lipids. These lipids contain a polyethylene glycol moiety, which defines the molecular weight of the lipids, as well as a fatty acid tail comprising 14 C-atoms. In a particular embodiment, said C14-PEG2000 lipid is based on dimyristoyl, i.e. having 2 C14 tails, such as selected from the list comprising: a (dimyristoyl-based)-PEG2000 lipid such as DMG-PEG2000 lipid (1,2-dimyristoyl-rac-glycero-3-methoxypolyethylene glycol-2000) or 2-Dimyristoyl-sn-Glycero-3-Phosphoethanolamine glycol-2000 (DMPE-PEG2000).

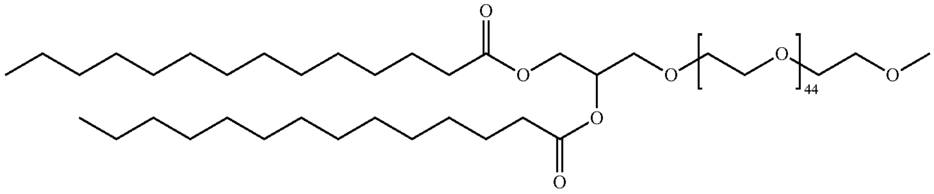

DMG-PEG2000

-continued

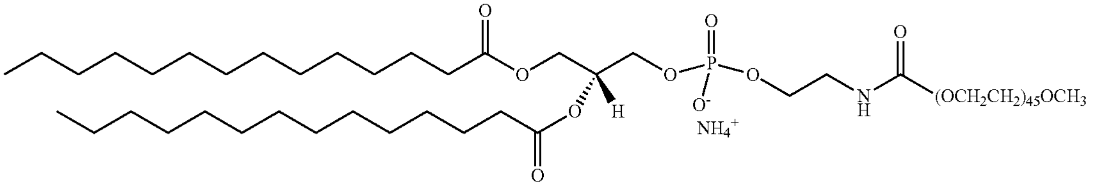

DMPE-PEG2000

In the context of the present invention the term "ionizable" (or alternatively cationic) in the context of a compound or lipid means the presence of any uncharged group in said compound or lipid which is capable of dissociating by yielding an ion (usually an $H^+$ ion) and thus itself becoming positively charged. Alternatively, any uncharged group in said compound or lipid may yield an electron and thus becoming negatively charged.

In the context of the present invention any type of ionizable lipid can suitably be used. Specifically, suitable ionizable lipids are ionizable amino lipids which comprise 2 identical or different tails linked via an S—S bond, each of said tails comprising an ionizable amine such as represented by

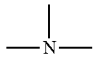

or

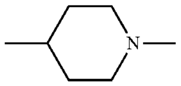

.

In a specific embodiment, said ionizable lipid is a compound of formula (I):

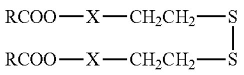

(I)

wherein:

RCOO is selected from the list comprising: myristoyl, α-D-Tocopherolsuccinoyl, linoleoyl and oleoyl; and X is selected from the list comprising:

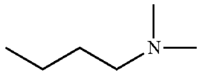

and

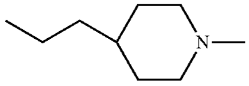

.

Such ionizable lipids may specifically be represented by anyone of the following formulae:

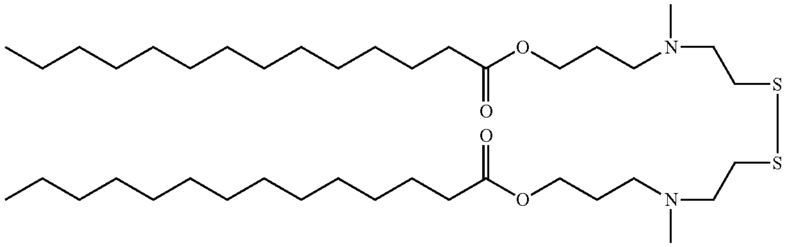

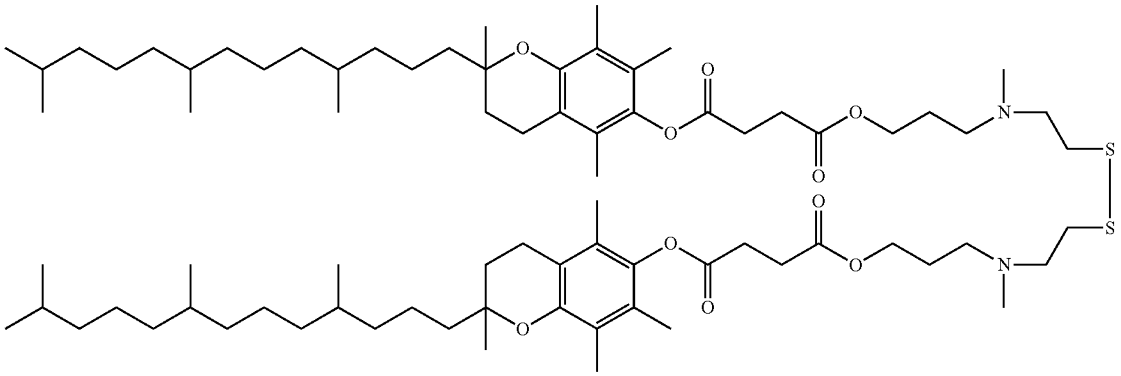

-continued

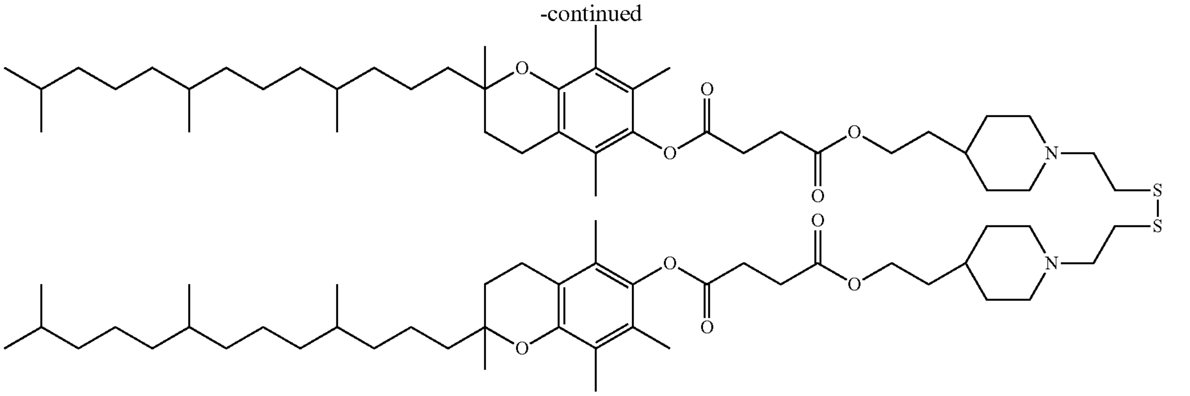

The latter of the above lipids represents Coatsome SS-EC, as used in the examples part.

More specifically, said ionizable lipid is a lipid of formula (I) wherein RCOO is α-D-Tocopherolsuccinoyl and X is

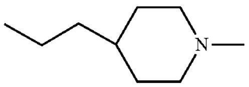

such as represented by

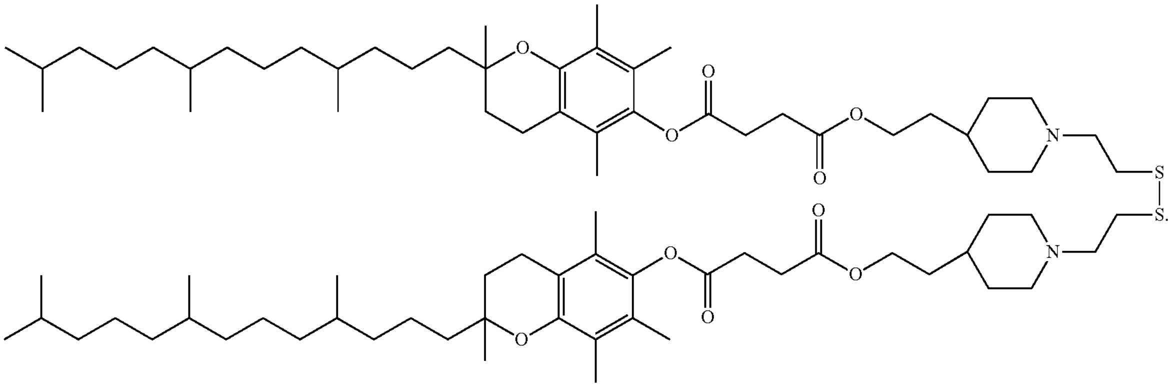 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

Other suitable ionizable lipids may be selected from 1,1-((2-(4-(2-((2-(bis(2-hydroxydodecyl)amino)ethyl)(2-hydroxydodecyl)amino)ethyl) piperazin-1-yl)ethyl) azanediyl) bis(dodecan-2-ol) (C12-200); and dilinoleylm-ethyl-4-dimethylaminobutyrate (DLin-MC3-DMA).

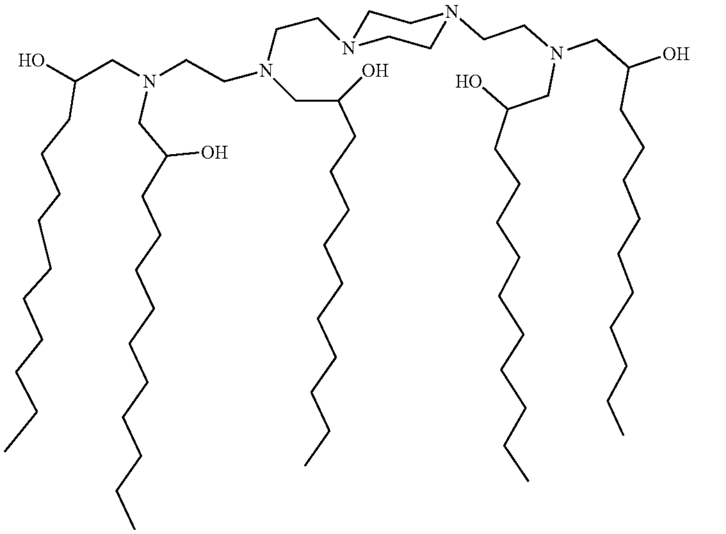

C12-200

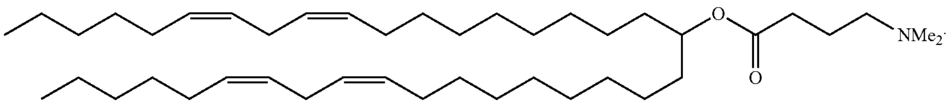

DLin-MC3-DMA

Hence, in a specific embodiment, the present invention provides a lipid nanoparticle comprising:

a compound of formula (I):

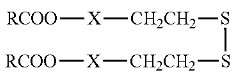

(I)

wherein:

RCOO is selected from the list comprising: myristoyl, α-D-Tocopherolsuccinoyl, linoleoyl and oleoyl; and X is selected from the list comprising:

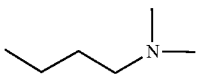

and

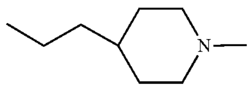

a phospholipid;

a sterol;

a PEG lipid; and one or more nucleic acid molecules; in particular mRNA molecules;

characterized in that said PEG lipid is a C14-PEG lipid;

said LNP comprises less than about 1 mol % of said PEG lipid;

the molar percentage of said ionizable lipid is about and between 50-70 mol %; and the molar percentage of said sterol is about or above 25 mol %.

Hence, in a specific embodiment, the present invention provides a lipid nanoparticle comprising:

a compound of formula (I):

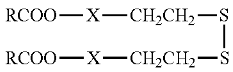

(I)

wherein:

RCOO is selected from the list comprising: myristoyl, α-D-Tocopherolsuccinoyl, linoleoyl and oleoyl; and X is selected from the list comprising:

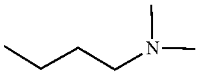

and

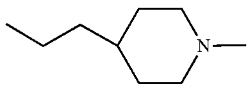

a phospholipid;

a sterol;

a PEG lipid; and one or more nucleic acid molecules; in particular mRNA molecules;

characterized in that said PEG lipid is a C14-PEG lipid;

said LNP comprises less than about 1 mol % of said PEG lipid;

the molar percentage of said ionizable lipid is about and between 50-60 mol %; and the molar percentage of said sterol is about or above 30 mol %.

In a preferred embodiment, said ionizable lipid is a lipid of formula (I) wherein RCOO is α-D-Tocopherolsuccinoyl and X is

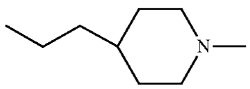

In the context of the present invention, the term “phospholipid” is meant to be a lipid molecule consisting of two hydrophobic fatty acid “tails” and a hydrophilic “head” consisting of a phosphate groups. The two components are most often joined together by a glycerol molecule, hence, the phospholipid of the present invention is preferably a glycerol-phospholipid. Furthermore, the phosphate group is often modified with simple organic molecules such as choline (i.e. rendering a phosphocholine) or ethanolamine (i.e. rendering a phosphoethanolamine).

Suitable phospholipids within the context of the invention can be selected from the list comprising: 1,2-Dioleoyl-sn-glycero-3-phosphoethanolamine (DOPE), 1,2-Dioleoyl-sn-glycero-3-phosphocholine (DOPC), 1,2-distearoyl-sn-glycero-3-phosphocholine (DSPC), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In a specific embodiment of the invention, when the phospholipid is selected to be DSPC, the ionizable lipid may advantageously be DLin-MC3-DMA.

In a more specific embodiment, said phospholipid is selected from the list comprising: 1,2-Dioleoyl-sn-glycero-3-phosphoethanolamine (DOPE), 1,2-Dioleoyl-sn-glycero-3-phosphocholine (DOPC), 1,2-distearoyl-sn-glycero-3-phosphocholine (DSPC), and mixtures thereof; in particular DOPE, DOPC and mixtures thereof.

Hence, in a specific embodiment, the present invention provides a lipid nanoparticle comprising:

an ionizable lipid of formula (I);

(I)

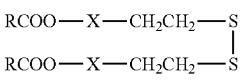

wherein:

RCOO is selected from the list comprising: myristoyl, α-D-Tocopherolsuccinoyl, linoleoyl and oleoyl; and X is selected from the list comprising:

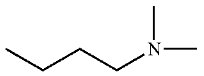

and

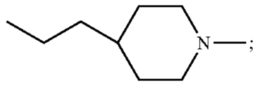

;

in particular, a lipid of formula (I) wherein RCOO is α-D-Tocopherolsuccinoyl and X is

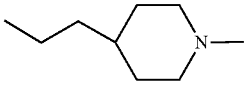

a phospholipid selected from DOPC and DOPE, or mixtures thereof;

a sterol;

a C14-PEG2000 lipid present at less than about 1 mol %; and one or more nucleic acid molecules; in particular mRNA molecules;

characterized in that the molar percentage of said ionizable lipid is about and between 50-70 mol %; and the molar percentage of said sterol is about or above 25 mol %.

Hence, in a specific embodiment, the present invention provides a lipid nanoparticle comprising:

an ionizable lipid of formula (I);

(I)

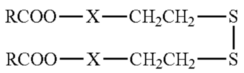

wherein:

RCOO is selected from the list comprising: myristoyl, α-D-Tocopherolsuccinoyl, linoleoyl and oleoyl; and X is selected from the list comprising:

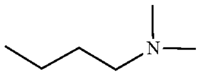

and

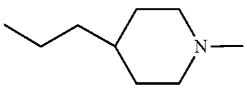

;

in particular, a lipid of formula (I) wherein RCOO is α-D-Tocopherolsuccinoyl and X is

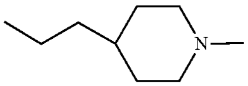

a phospholipid selected from DOPC and DOPE, or mixtures thereof;

a sterol;

a C14-PEG2000 lipid present at less than about 1 mol %; and one or more nucleic acid molecules; in particular mRNA molecules;

characterized in that the molar percentage of said ionizable lipid is about and between 50-60 mol %; and the molar percentage of said sterol is about or above 30 mol %.

In the context of the present invention, the term "sterol", also known as steroid alcohol, is a subgroup of steroids that occur naturally in plants, animal and fungi, or can be produced by some bacteria. In the context of the present invention, any suitable sterol may be used, such as selected from the list comprising cholesterol, ergosterol, campesterol, oxysterol, antrosterol, desmosterol, nicasterol, sitosterol and stigmasterol; preferably cholesterol.

Hence, in a specific embodiment, the present invention provides a lipid nanoparticle comprising:

an ionizable lipid of formula (I);

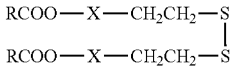
(I)

wherein:

RCOO is selected from the list comprising: myristoyl, α-D-Tocopherolsuccinoyl, linoleoyl and oleoyl; and X is selected from the list comprising:

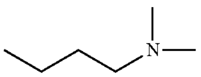
and
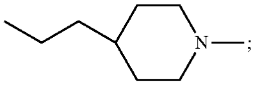

in particular, a lipid of formula (I) wherein RCOO is α-D-Tocopherolsuccinoyl and X is

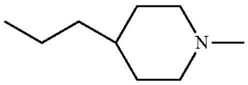

a phospholipid selected from DOPC and DOPE, or mixtures thereof;

cholesterol;

a C14-PEG2000 lipid present at less than about 1 mol %; and one or more nucleic acid molecules; in particular mRNA molecules characterized in that the molar percentage of said ionizable lipid is about and between 50-70 mol %; and the molar percentage of said sterol is about or above 25 mol %.

Hence, in a specific embodiment, the present invention provides a lipid nanoparticle comprising:

an ionizable lipid of formula (I);

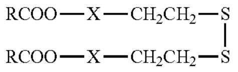
(I)

wherein:

RCOO is selected from the list comprising: myristoyl, α-D-Tocopherolsuccinoyl, linoleoyl and oleoyl; and X is selected from the list comprising:

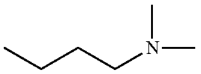
and
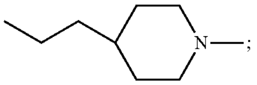

in particular, a lipid of formula (I) wherein RCOO is α-D-Tocopherolsuccinoyl and X is

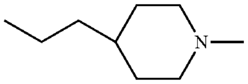

a phospholipid selected from DOPC and DOPE, or mixtures thereof;

cholesterol;

a C14-PEG2000 lipid present at less than about 1 mol %; and one or more nucleic acid molecules; in particular mRNA molecules characterized in that the molar percentage of said ionizable lipid is about and between 50-60 mol %; and the molar percentage of said sterol is about or above 30 mol %.

In a very specific embodiment of the present invention, said lipid nanoparticle comprises:

an ionizable lipid of formula (I);

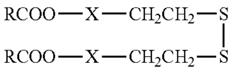
(I)

wherein:

RCOO is selected from the list comprising: myristoyl, α-D-Tocopherolsuccinoyl, linoleoyl and oleoyl; and X is selected from the list comprising:

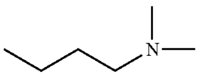
and
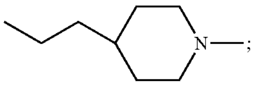

in particular, a lipid of formula (I) wherein RCOO is α-D-Tocopherolsuccinoyl and X is

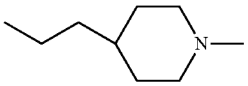

a phospholipid selected from DOPC and DOPE, or mixtures thereof;

cholesterol;

a DMG-PEG2000 lipid present at less than about 1 mol %; and one or more nucleic acid molecules; in particular mRNA molecules;

characterized in that the molar percentage of said ionizable lipid is about and between 50-70 mol %; and the molar percentage of said sterol is about or above 25 mol %.

In a very specific embodiment of the present invention, said lipid nanoparticle comprises:

an ionizable lipid of formula (I);

(I)

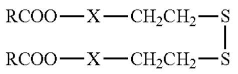

wherein:

RCOO is selected from the list comprising: myristoyl, α-D-Tocopherolsuccinoyl, linoleoyl and oleoyl; and X is selected from the list comprising:

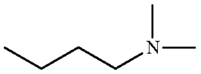 and 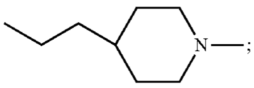;

in particular, a lipid of formula (I) wherein RCOO is α-D-Tocopherolsuccinoyl and X is

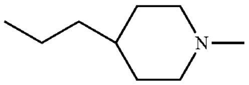

a phospholipid selected from DOPC and DOPE, or mixtures thereof;

cholesterol;

a DMG-PEG2000 lipid present at less than about 1 mol %; and one or more nucleic acid molecules; in particular mRNA molecules;

characterized in that the molar percentage of said ionizable lipid is about and between 50-60 mol %; and the molar percentage of said sterol is about or above 30 mol %.

We have moreover found that the immunogenic effects of the LNPs of the present invention can even be further increased by using a combination of low levels of PEG lipids with relatively high levels of ionizable lipid (i.e. between 50-70 mol %; such as between 50-65 mol % or between 55-60 mol %) and relatively low levels of phospholipids (i.e. less than about 10 mol %), accordingly for LNPs having relatively high ratio's of ionizable lipid:phospholipid (i.e. 5:1-10:1; alternatively between about 6:1 and about 11:1). High levels of ionizable lipids may thus for example be about 50 mol %, about 51 mol %, about 52 mol %, about 53 mol %, about 54 mol %, about 55 mol %, about 56 mol %, about 57 mol %, about 58 mol %, about 59 mol %, about 60 mol %, about 61 mol %, about 62 mol %, about 63 mol %, about 64 mol %, about 65 mol %; about 66 mol %, about 67 mol %, about 68 mol %, about 69 mol %; about 70 mol %.

Accordingly, in another particular embodiment, the molar percentage of said phospholipid is about and between 5-15 mol % of a phospholipid; in particular about and between 5-10 mol %; more in particular less than about 10 mol %; such as about 9 mol %, about 8 mol %, about 7 mol %, about 6 mol %; about 5 mol %; preferably about 5 mol %.

In a specific embodiment of the present invention, said LNP comprises a ratio of ionizable lipid to phospholipid of about or above 5:1; preferably about or above 6:1; more preferably above 8:1, most preferably about 10:1; alternatively between about 6:1 and 11:1; most preferably about 11:1, such as about 10.76:1.

In yet a further embodiment of the present invention, the molar percentage of said ionizable lipid is about and between 50-70 mol %; such as between 50-65 mol %, in particular about and between 55-60 mol %.

Sterol is typically used as a balancer lipid and in some embodiments amounts to about or above 25 mol %, such as about 25 mol %, about 26 mol %, about 27 mol %, about 28 mol % about 29 mol %. Alternatively it amounts to about or above 30 mol %; such as about 30 mol %; about 31 mol %; about 32 mol %; about 33 mol %; about 34 mol %; about 35 mol %, . . . . In a specific embodiment the amount of cholesterol is about and between 25 mol % and 29 mol %. Accordingly, the concentration of sterol is typically weighed against the concentrations of the other lipids in order to make up the full 100%. Therefore, the amount of sterol may be calculated as 100 mol % minus the mol % of phospholipid minus the mol % of PEG lipid minus the mol % of ionizable lipid.

Hence, in a specific embodiment of the present invention one or more of the following applies:

said LNP comprises about and between 50 mol % and 70 mol % of said ionizable lipid; alternatively about and between 50-65 mol %; or 50-60 mol %; such as about and between 55-60 mol %;

said LNP comprises about and between 5 mol % and 15 mol % of said phospholipid; preferably less than about 10 mol %; most preferably about 5 mol %;

said LNP comprises about and between 0.5 mol % and 0.9 mol % of said PEG lipid; balanced by the amount of said sterol.

Therefore, in a very specific embodiment of the present invention, said LNP comprises:

about 50-70 mol % of an ionizable lipid of formula (I);

(I)

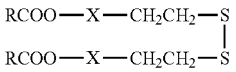

wherein:

RCOO is selected from the list comprising: myristoyl, α-D-Tocopherolsuccinoyl, linoleoyl and oleoyl; and X is selected from the list comprising:

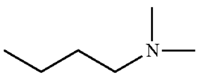 and 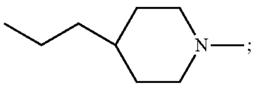;

in particular, a lipid of formula (I) wherein RCOO is α-D-Tocopherolsuccinoyl and X is

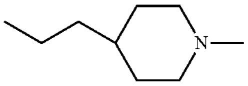

about 5-15 mol % of a phospholipid selected from DOPC and DOPE, or mixtures thereof;

cholesterol to balance;

about 0.5-0.9 mol % of DMG-PEG2000 lipid; and one or more nucleic acid molecules, in particular mRNA molecules.

Therefore, in a very specific embodiment of the present invention, said LNP comprises:

about 50-60 mol % of an ionizable lipid of formula (I);

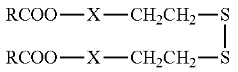

(I)

wherein:

RCOO is selected from the list comprising: myristoyl, α-D-Tocopherolsuccinoyl, linoleoyl and oleoyl; and X is selected from the list comprising:

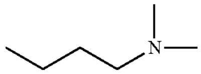

and

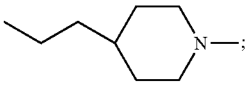

;

in particular, a lipid of formula (I) wherein RCOO is α-D-Tocopherolsuccinoyl and X is

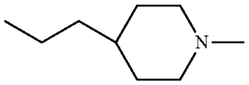

about 5-15 mol % of a phospholipid selected from DOPC and DOPE, or mixtures thereof;

cholesterol to balance;

about 0.5-0.9 mol % of DMG-PEG2000 lipid; and one or more nucleic acid molecules, in particular mRNA molecules.

Where in the context of the present invention mol % is used, it is meant to be the mol % of the specified component with respect to the empty nanoparticle, i.e. without nucleic acids. This means that the mol % of a component is calculated with respect to the total amount of ionizable lipids, phospholipids, sterols and PEG lipids, present in said LNP.

In a specific embodiment of the present invention, said LNP comprises:

about 50-60 mol % of said ionizable lipid;

about 5-15 mol % of said phospholipid;

about 0.5-0.9 mol % of said DMG-PEG2000 lipid; and balanced by the amount of said sterol.

In a very specific embodiment of the present invention, said LNP comprises:

about 56.5 mol % of said ionizable lipid;

about 5.25 mol % of DOPE;

about 37.75 mol % of cholesterol; and about 0.5 mol % of DMG-PEG2000.

In another very specific embodiment of the present invention, said LNP comprises:

about 50 mol % of said ionizable lipid;

about 10 mol % of DOPE;

about 39.5 mol % of cholesterol; and about 0.5 mol % of DMG-PEG2000.

In a another very specific embodiment of the present invention, said LNP comprises:

about 50 mol % of said ionizable lipid;

about 11 mol % of DOPE;

about 38.5 mol % of cholesterol; and about 0.5 mol % of DMG-PEG2000.

In a yet another very specific embodiment of the present invention, said LNP comprises:

about 50 mol % of said ionizable lipid;

about 7.76 mol % of DOPE;

about 41.66 mol % of cholesterol; and about 0.58 mol % of DMG-PEG2000.

In another very specific embodiment of the present invention, said LNP comprises:

about 65 mol % of said ionizable lipid;

about 9.5 mol % of DOPE;

about 25 mol % of cholesterol; and about 0.5 mol % of DMG-PEG2000.

Therefore, in a very specific embodiment of the present invention, said LNP comprises:

about 50 mol % of an ionizable lipid of formula (I);

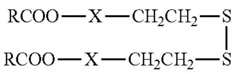

(I)

wherein:

RCOO is α-D-Tocopherolsuccinoyl and X is

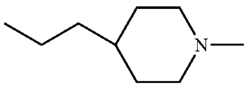

about 10 mol % of a phospholipid selected from DOPC and DOPE, or mixtures thereof;

about 39.5 mol % of cholesterol;

about 0.5 mol % of DMG-PEG2000 lipid; and one or more nucleic acid molecules, in particular mRNA molecules.

In another very specific embodiment of the present invention, said LNP comprises:

about 56.5 mol % of an ionizable lipid of formula (I);

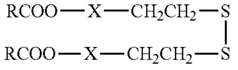

(I)

wherein:

RCOO is α-D-Tocopherolsuccinoyl and X is

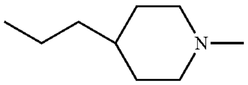

about 5.25 mol % of a phospholipid selected from DOPC and DOPE, or mixtures thereof;

about 37.75 mol % of cholesterol;

about 0.5 mol % of DMG-PEG2000 lipid; and one or more nucleic acid molecules, in particular mRNA molecules.

In another very specific embodiment of the present invention, said LNP comprises:

about 65 mol % of an ionizable lipid of formula (I);

(I)

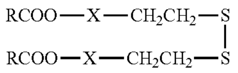

wherein:

RCOO is α-D-Tocopherolsuccinoyl and X is

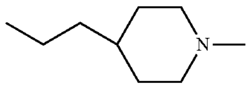

about 9.5 mol % of a phospholipid selected from DOPC and DOPE, or mixtures thereof;

about 25 mol % of cholesterol;

about 0.5 mol % of DMG-PEG2000 lipid; and one or more nucleic acid molecules, in particular mRNA molecules.

In another very specific embodiment of the present invention, said LNP comprises:

about 50 mol % of an ionizable lipid of formula (I);

(I)

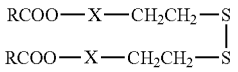

wherein:

RCOO is α-D-Tocopherolsuccinoyl and X is

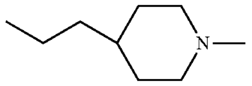

about 11 mol % of a phospholipid selected from DOPC and DOPE, or mixtures thereof;

about 38.5 mol % of cholesterol;

about 0.5 mol % of DMG-PEG2000 lipid; and one or more nucleic acid molecules, in particular mRNA molecules.

In another very specific embodiment of the present invention, said LNP comprises:

about 50 mol % of an ionizable lipid of formula (I);

(I)

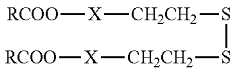

wherein:

RCOO is α-D-Tocopherolsuccinoyl and X is

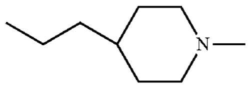

about 7.76 mol % of a phospholipid selected from DOPC and DOPE, or mixtures thereof;

about 41.66 mol % of cholesterol;

about 0.58 mol % of DMG-PEG2000 lipid; and one or more nucleic acid molecules, in particular mRNA molecules.

The composition of other particularly suitable LNP's in the context of the invention is represented in table 1.

TABLE 1

Composition of suitable LNP's

| No | Ionizable Lipid (mol %) | Phospholipid (mol %) | Cholesterol (mol %) | C14-PEG2000 Lipid (mol %) |
|---|---|---|---|---|
| 1 | 50 | 10.0 | 39.5 | 0.5 |
| 2 | 50 | 8.3 | 41.2 | 0.5 |
| 3 | 50 | 7.1 | 42.4 | 0.5 |
| 4 | 50 | 6.3 | 43.3 | 0.5 |
| 5 | 50 | 5.6 | 43.9 | 0.5 |
| 6 | 50 | 5.0 | 44.5 | 0.5 |
| 7 | 50 | 10.0 | 39.3 | 0.7 |
| 8 | 50 | 8.3 | 41.0 | 0.7 |
| 9 | 50 | 7.1 | 42.2 | 0.7 |
| 10 | 50 | 6.3 | 43.1 | 0.7 |
| 11 | 50 | 5.6 | 43.7 | 0.7 |
| 12 | 50 | 5.0 | 44.3 | 0.7 |
| 13 | 50 | 10.0 | 39.1 | 0.9 |
| 14 | 50 | 8.3 | 40.8 | 0.9 |
| 15 | 50 | 7.1 | 42.0 | 0.9 |
| 16 | 50 | 6.3 | 42.9 | 0.9 |
| 17 | 50 | 5.6 | 43.5 | 0.9 |
| 18 | 50 | 5.0 | 44.1 | 0.9 |
| 19 | 55 | 11.0 | 33.5 | 0.5 |
| 20 | 55 | 9.2 | 35.3 | 0.5 |
| 21 | 55 | 7.9 | 36.6 | 0.5 |
| 22 | 55 | 6.9 | 37.6 | 0.5 |
| 23 | 55 | 6.1 | 38.4 | 0.5 |
| 24 | 55 | 5.5 | 39.0 | 0.5 |
| 25 | 55 | 11.0 | 33.3 | 0.7 |
| 26 | 55 | 9.2 | 35.1 | 0.7 |
| 27 | 55 | 7.9 | 36.4 | 0.7 |
| 28 | 55 | 6.9 | 37.4 | 0.7 |
| 29 | 55 | 6.1 | 38.2 | 0.7 |
| 30 | 55 | 5.5 | 38.8 | 0.7 |
| 31 | 55 | 11.0 | 33.1 | 0.9 |
| 32 | 55 | 9.2 | 34.9 | 0.9 |
| 33 | 55 | 7.9 | 36.2 | 0.9 |
| 34 | 55 | 6.9 | 37.2 | 0.9 |
| 35 | 55 | 6.1 | 38.0 | 0.9 |
| 36 | 55 | 5.5 | 38.6 | 0.9 |
| 37 | 60 | 12.0 | 27.5 | 0.5 |
| 38 | 60 | 10.0 | 29.5 | 0.5 |
| 39 | 60 | 8.6 | 30.9 | 0.5 |
| 40 | 60 | 7.5 | 32.0 | 0.5 |
| 41 | 60 | 6.7 | 32.8 | 0.5 |
| 42 | 60 | 6.0 | 33.5 | 0.5 |
| 43 | 60 | 12.0 | 27.3 | 0.7 |
| 44 | 60 | 10.0 | 29.3 | 0.7 |
| 45 | 60 | 8.6 | 30.7 | 0.7 |
| 46 | 60 | 7.5 | 31.8 | 0.7 |
| 47 | 60 | 6.7 | 32.6 | 0.7 |
| 48 | 60 | 6.0 | 33.3 | 0.7 |
| 49 | 60 | 12.0 | 27.1 | 0.9 |
| 50 | 60 | 10.0 | 29.1 | 0.9 |
| 51 | 60 | 8.6 | 30.5 | 0.9 |
| 52 | 60 | 7.5 | 31.6 | 0.9 |
| 53 | 60 | 6.7 | 32.4 | 0.9 |
| 54 | 60 | 6.0 | 33.1 | 0.9 |
| 55 | 60 | 12.0 | 27.5 | 0.5 |
| 56 | 60 | 10.0 | 29.5 | 0.5 |
| 57 | 60 | 8.6 | 30.9 | 0.5 |
| 58 | 60 | 7.5 | 32.0 | 0.5 |
| 59 | 60 | 6.7 | 32.8 | 0.5 |
| 60 | 60 | 6.0 | 33.5 | 0.5 |
| 61 | 60 | 12.0 | 27.3 | 0.7 |
| 62 | 60 | 10.0 | 29.3 | 0.7 |
| 63 | 60 | 8.6 | 30.7 | 0.7 |

TABLE 1-continued

Composition of suitable LNP's

| No | Ionizable Lipid (mol %) | Phospholipid (mol %) | Cholesterol (mol %) | C14-PEG2000 Lipid (mol %) |
|---|---|---|---|---|
| 64 | 60 | 7.5 | 31.8 | 0.7 |
| 65 | 60 | 6.7 | 32.6 | 0.7 |
| 66 | 60 | 6.0 | 33.3 | 0.7 |
| 67 | 60 | 12.0 | 27.1 | 0.9 |
| 68 | 60 | 10.0 | 29.1 | 0.9 |
| 69 | 60 | 8.6 | 30.5 | 0.9 |
| 70 | 60 | 7.5 | 31.6 | 0.9 |
| 71 | 60 | 6.7 | 32.4 | 0.9 |
| 72 | 60 | 6.0 | 33.1 | 0.9 |
| 73 | 65 | 10.0 | 24.5 | 0.5 |
| 74 | 65 | 8.3 | 26.2 | 0.5 |
| 75 | 65 | 7.1 | 27.4 | 0.5 |
| 76 | 65 | 6.3 | 28.2 | 0.5 |
| 77 | 65 | 5.6 | 28.9 | 0.5 |
| 78 | 65 | 5.0 | 29.5 | 0.5 |
| 79 | 65 | 10.0 | 24.3 | 0.7 |
| 80 | 65 | 8.3 | 26.0 | 0.7 |
| 81 | 65 | 7.1 | 27.2 | 0.7 |
| 82 | 65 | 6.3 | 28.0 | 0.7 |
| 83 | 65 | 5.6 | 28.7 | 0.7 |
| 85 | 65 | 5.0 | 29.3 | 0.7 |
| 86 | 65 | 10.0 | 24.1 | 0.9 |
| 87 | 65 | 8.3 | 25.8 | 0.9 |
| 88 | 65 | 7.1 | 27.0 | 0.9 |
| 89 | 65 | 6.3 | 27.8 | 0.9 |
| 90 | 65 | 5.6 | 28.5 | 0.9 |
| 91 | 65 | 5.0 | 29.1 | 0.9 |

Other particularly suitable LNP's are characterized by an ionizable lipid/phospholipid/sterol/C14-PEG2000 lipid ratio of:

50/10/39.5/0.5
56.5/5/38/0.5
50/11/138.5/0.5
50/7.76/41.66/0.58
65/9.5/25/0.5

The inventors have found that the LNP's of the present invention are particularly suitable for the immunogenic delivery of nucleic acids. Hence the present invention provides LNP's comprising one or more nucleic acid molecules, such as DNA or RNA, more specifically mRNA.

The amount of nucleic acid in said LNP's is typically represented by the molar ratio, i.e. the ratio of cationic lipid (ionizable lipid) to RNA phosphates. In the context of the present invention, the molar ratio of the LNP's is about and between 4:1 and 16:1.

The amount of nucleic acid in said LNP's can alternatively be represented by the N/P ratio, i.e. the ratio of nitrogen atoms in ionizable lipids to phosphate groups in the nucleic acids. In the context of the present invention, the N/P ratio of the LNP's is about and between 4:1 and 16:1.

A "nucleic acid" in the context of the invention is a deoxyribonucleic acid (DNA) or preferably a ribonucleic acid (RNA), more preferably mRNA. Nucleic acids include according to the invention genomic DNA, cDNA, mRNA, recombinantly produced and chemically synthesized molecules. A nucleic acid may according to the invention be in the form of a molecule which is single stranded or double stranded and linear or closed covalently to form a circle. A nucleic acid can be employed for introduction into, i.e. transfection of cells, for example, in the form of RNA which can be prepared by in vitro transcription from a DNA template. The RNA can moreover be modified before application by stabilizing sequences, capping, and/or polyadenylation.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs. Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' untranslated region (5'-UTR), a protein or peptide coding region and a 3' untranslated region (3-UTR). mRNA has a limited halftime in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In a specific embodiment of the present invention, said mRNA molecules are mRNA molecules encoding immune modulating proteins.

In the context of the present invention, the term "mRNA molecules encoding immune modulating proteins" is meant to be mRNA molecules encoding proteins that modify the functionality of antigen presenting cells; more in particular dendritic cells. Such molecules may be selected from the list comprising CD40L, CD70, caTLR4, IL-12p70, L-selectin, CCR7, and/or 4-1BBL, ICOSL, OX40L, IL-21; more in particular one or more of CD40L, CD70 and caTLR4. A preferred combination of immunostimulatory factors used in the methods of the invention is CD40L and caTLR4 (i.e. "DiMix"). In another preferred embodiment, the combination of CD40L, CD70 and caTLR4 immunostimulatory molecules is used, which is herein also named "TriMix".

In another specific embodiment, said mRNA molecules are mRNA molecules encoding antigen- and/or disease-specific proteins.

According to the present invention, the term "antigen" comprises any molecule, preferably a peptide or protein, which comprises at least one epitope that will elicit an immune response and/or against which an immune response is directed; accordingly, the term antigen is also meant to encompass minimal epitopes from antigens. A "minimal epitope" as defined herein is meant to be the smallest structure which is capable of eliciting an immune response. Preferably, an antigen in the context of the present invention is a molecule which, optionally after processing, induces an immune response, which is preferably specific for the antigen or cells expressing the antigen. In particular, an "antigen" relates to a molecule which, optionally after processing, is presented by MHC molecules and reacts specifically with T lymphocytes (T cells).

In a specific embodiment, the antigen is a target-specific antigen which can be a tumor antigen, or a bacterial, viral or fungal antigen. Said target-specific antigen can be derived from either one of: total mRNA isolated from (a) target cell(s), one or more specific target mRNA molecules, protein lysates of (a) target cell(s), specific proteins from (a) target cell(s), or a synthetic target-specific peptide or protein and synthetic mRNA or DNA encoding a target-specific antigen or its derived peptides.

To avoid any misunderstanding, the LNP's of the present invention may comprise a single mRNA molecule, or they may comprise multiple mRNA molecules, such as a combination of one or more mRNA molecules encoding immune modulating proteins and/or one or more mRNA molecules encoding antigen- and/or disease-specific proteins.

In a very specific embodiment, said mRNA molecules encoding immunomodulatory molecules may be combined with one or more mRNA molecules encoding antigen- and/or disease-specific proteins. For example, the LNP's of the present invention may comprise mRNA molecules encoding the immunostimulatory molecules CD40L, CD70 and/or caTLR4 (such as Dimix or Trimix); in combination with one or more mRNA molecules encoding antigen- and/or disease-specific proteins. Thus, in a very specific embodiment, the LNP's of the present invention comprise an mRNA molecule encoding CD40L, CD70 and/or caTLR4; in combination with one or more mRNA molecules encoding antigen- and/or disease-specific proteins.

In a further aspect, the present invention provides a pharmaceutical composition comprising one or more LNP's as defined herein. Such pharmaceutical compositions are particularly suitable as a vaccine. Thus, the invention also provides a vaccine comprising one or more LNP's according to the present invention.

In the context of the present invention, the term "vaccine" as used herein is meant to be any preparation intended to provide adaptive immunity (antibodies and/or T cell responses) against a disease. To that end, a vaccine as meant herein contains at least one mRNA molecule encoding an antigen to which an adaptive immune response is mounted. This antigen can be present in the format of a weakened or killed form of a microbe, a protein or peptide, or an antigen encoding a nucleic acid. An antigen in the context of this invention is meant to be a protein or peptide recognized by the immune system of a host as being foreign, thereby stimulating the production of antibodies against is, with the purpose of combating such antigens. Vaccines can be prophylactic (example: to prevent or ameliorate the effects of a future infection by any natural or "wild" pathogen), or therapeutic (example, to actively treat or reduce the symptoms of an ongoing disease). The administration of vaccines is called vaccination.

The vaccine of the invention may be used for inducing an immune response, in particular an immune response against a disease-associated antigen or cells expressing a disease-associated antigen, such as an immune response against cancer. Accordingly, the vaccine may be used for prophylactic and/or therapeutic treatment of a disease involving a disease-associated antigen or cells expressing a disease-associated antigen, such as cancer. Preferably said immune response is a T cell response. In one embodiment, the disease-associated antigen is a tumor antigen. The antigen encoded by the RNA comprised in the nanoparticles described herein preferably is a disease-associated antigen or elicits an immune response against a disease-associated antigen or cells expressing a disease-associated antigen.

The LNP's and vaccines of the present invention are specifically intended for intravenous administration, i.e. the infusion of liquid substance directly into a vein. The intravenous route is the fastest way to deliver fluids and medications throughout the body, i.e. systemically. The present invention thus provides intravenous vaccines, as well as the use of the disclosed vaccines and LNP's for intravenous administration. The vaccines and LNP's of the present invention can thus be administered intravenously. The present invention also provides the use of the vaccines and LNP's according to the present invention; wherein the vaccine is administered intravenously.

It was particularly found that the immunogenicity of the LNPs of the present invention increases upon multiple immunizations. Therefore, in a particular embodiment, the LNPs as defined herein are for use in vaccination purposes, wherein the LNPs are administered at least twice, preferably at least 3 times within a particular interval.

The present invention also provides the LNP's, pharmaceutical compositions and vaccines according to this invention for use in human or veterinary medicine. The use of the LNP's, pharmaceutical compositions and vaccines according to this invention for human or veterinary medicine is also intended. Finally, the invention provides a method for the prophylaxis and treatment of human and veterinary disorders, by administering the LNP's, pharmaceutical compositions and vaccines according to this invention to a subject in need thereof.

The present invention further provides the use of an LNP, a pharmaceutical composition or a vaccine according to the present invention for the immunogenic delivery of said one or more nucleic acid molecules. As such the LNP's, pharmaceutical compositions and vaccine of the present invention are highly useful in the treatment several human and veterinary disorders. Thus, the present invention provides the LNP's, pharmaceutical compositions and vaccines of the present invention for use in the treatment of cancer or infectious diseases.

The lipid nanoparticles of the present invention may be prepared in accordance with the protocols as specified in the Examples part. More generally, the LNP's may be prepared using a method comprising:

- preparing a first alcoholic composition comprising said ionizable lipid, said phospholipid, said sterol, said PEG lipid, and a suitable alcoholic solvent;
- preparing a second aqueous composition comprising said one or more nucleic acids and an aqueous solvent;
- mixing said first and second composition in a microfluidic mixing device.

In further detail, the lipid components are combined in suitable concentrations in an alcoholic vehicle such as ethanol. Thereto, an aqueous composition comprising the nucleic acid is added, and subsequently loaded in a microfluidic mixing device.

The aim of microfluidic mixing is to achieve thorough and rapid mixing of multiple samples (i.e. lipid phase and nucleic acid phase) in a microscale device. Such sample mixing is typically achieved by enhancing the diffusion effect between the different species flows. Thereto several microfluidic mixing devices can be used, such as for example reviewed in Lee et al., 2011. A particularly suitable microfluidic mixing device according to the present invention is the NanoAssemblr from Precision Nanosystems.

Other technologies suitable for preparing the LNP's of the present invention include dispersing the components in a suitable dispersing medium, for example, aqueous solvent and alcoholic solvent, and applying one or more of the following methods: ethanol dilution method, a simple hydration method, sonication, heating, vortex, an ether injecting method, a French press method, a cholic acid method, a Ca fusion method, a freeze-thaw method, a reversed-phase evaporation method, T-junction mixing, Microfluidic Hydrodynamic Focusing, Staggered Herringbone Mixing, and the like.

EXAMPLES

Materials and Methods for Examples 1-3

Mice

Female C57BL/6 Mice were purchased from Charles River Laboratories (France) and housed in individually vented cages with standard bedding material and cage enrichment. The animals were maintained and treated in accordance to the institutional (Vrije Universiteit Brussel) and European Union guidelines for animal experimentation. Mice had ad libitum access to food and water. Experiments started when mice were 6 to 10 weeks old. Mice received intravenous injections via the tail vein with 10 μg mRNA in LNP's (in a volume of 200 μL). Control mice were injected with 200 μl of TBS (Tris Buffered Saline) at identical time intervals. Weight of mice was monitored every 2 days.

In case of vaccination with ADPGK Synthetic Long Peptide (SLP), mice were injected intraperitoneally with a combination of 50 μg ADPGK SLP (GIPVHLELASMTNMELMSSIVHQQVFPT, (SEQ ID No 3) Genscript), 50 μg anti-CD40 Mab (Clone FJK45, BioXCell) and 100 μg pIC HMW (InvivoGen) in 200 μl of PBS at identical time intervals.

mRNA Synthesis and Purification

Capped, non-nucleoside modified E7 and ADPGK mRNA was prepared by eTheRNA by in vitro transcription (IVT) from the eTheRNA plasmid pEtherna, in accordance with the protocol as described in WO2015071295. The sequence encoding the HPV16-E7 or ADPGK protein was cloned in-frame between the signal sequence and the transmembrane and cytoplasmic regions of human DC-LAMP. This chimeric gene was cloned in the pEtherna plasmid that was enriched with a translation enhancer at the 5' end and an RNA stabilizing sequence at the 3' end. After IVT, dsRNA was removed by cellulose purification. Cellulose powder was purchased from Sigma and washed in 1×STE (Sodium Chloride-Tris-EDTA) buffer with 16% ethanol. IVT mRNA (in 1×STE buffer with 16% ethanol) was added to the washed cellulose pellet and shaken at room temperature for 20 minutes. This solution is then brought over a vacuum filter (Corning). The eluate contains the ssRNA fraction and was used for all experiments. mRNA quality was monitored by capillary gel electrophoresis (Agilent, Belgium).

Generation of mRNA Lipid-Based Nanoparticles

Lipid based nanoparticles are produced by microfluidic mixing of an mRNA solution in sodium acetate buffer (100 mM, pH4) and lipid solution in a 2:1 volume ratio at a speed of 9 mL/min using the NanoAssemblr Benchtop (Precision Nanosystems). The lipid solution contained a mixture of CoatsomeSS-EC (NOF corporation), DOPE (Avanti), Cholesterol (Sigma) and DMG-PEG2000 (C14 lipid) (Sunbright GM-020, NOF corporation). The 4 lipids were mixed at different molar ratios. LNP's were dialyzed against TBS (10000 times more TBS volume than LNP volume) using slide-a-lyzer dialysis cassettes (20K MWCO, 3 mL, ThermoFisher).

Flow Cytometry

Blood was collected from treated and control mice approximately 6 days after immunization. Red blood cells were lysed and the remaining white blood cells were stained with APC labelled $E7_{(RAHYNIVTF)}$-tetramer (SEQ ID No 1) or ADPGK (ASMTNMELM)-tetramer (SEQ ID No 2) according to the manufacturer's instructions (MBL International). Excess tetramer was washed away. Hereafter, an antibody mixture for surface molecules (listed in table 2) was added to the cells and incubated for 30 minutes at 4° C. Data was acquired on an LSR Fortessa cytometer and analyzed with Flow Jo Software.

Results

Example 1

Mice received three intravenous immunizations with E7 mRNA LNPs composed of SS-EC/DOPE/chol/DMG-PEG2000 at the indicated molar ratios. The percentages of E7-specific CD8 T cells elicited by the respective mRNA LNP compositions were assessed in blood by flow cytometry after each immunization. As evident from FIG. 1, mRNA LNPs formulated at a 0.5 mol % DMG-PEG2000 elicited a much higher E7-specific CD8 T cell response compared to mRNA LNPs formulated at a 1 mol % DMG-PEG2000.

Example 2

Figure 2:
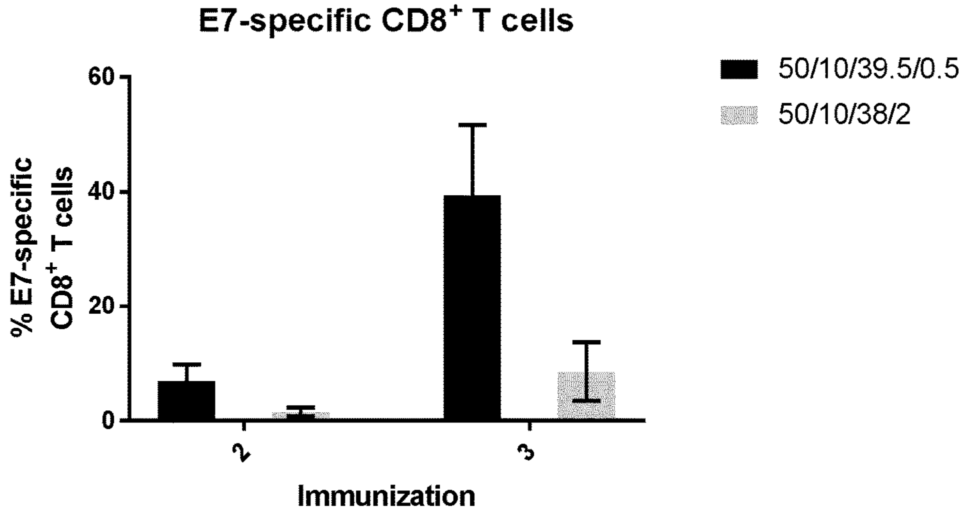
FIG. 2: Shows the results of three intravenous immunizations with E7 mRNA LNPs composed of SS-EC/DOPE/chol/DMG-PEG2000 at the indicated molar ratios.

Mice received three intravenous immunizations with E7 mRNA LNPs composed of SS-EC/DOPE/chol/DMG-PEG2000 at the indicated molar ratios. The percentages of E7-specific CD8 T cells elicited by the respective mRNA LNP compositions were assessed in blood by flow cytometry after each immunization. As evident from FIG. 2, mRNA LNPs formulated at a 0.5 mol % DMG-PEG2000 elicited a much higher E7-specific CD8 T cell response compared to mRNA LNPs formulated at a 2 mol % DMG-PEG2000, an effect, which was even more pronounced after 3 immunizations.

Example 3

Figure 3:
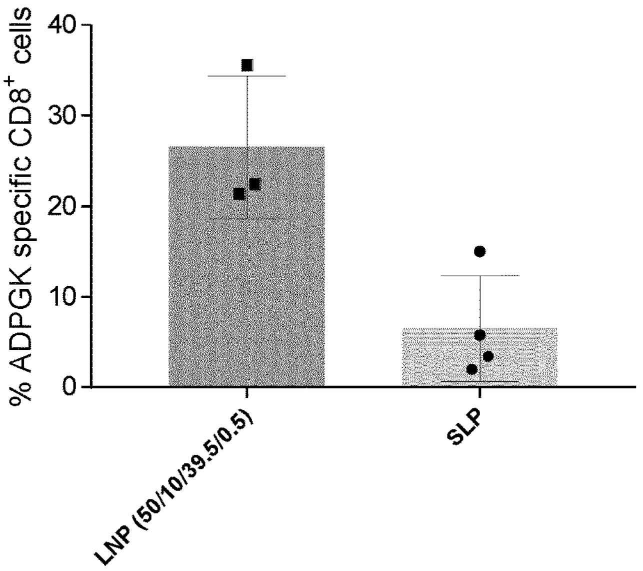
FIG. 3: Shows the results of four intravenous administrations with 10 μg ADPGK mRNA packaged in a low percentage PEG LNP (50/10/39.5/0.5 ionizable lipid/DOPE/cholesterol/PEG-lipid) or with 50 μg ADPGK synthetic long peptide (SLP).

Mice received four intravenous administrations with 10 μg ADPGK mRNA packaged in a low percentage PEG LNP (50/10/39.5/0.5 ionizable lipid/DOPE/cholesterol/PEG-lipid) or with 50 μg ADPGK synthetic long peptide (SLP). Percentage of ADPGK-specific $CD8^+$ T cells in blood was determined 6 days after the fourth immunization. mRNA LNPs formulated at the 0.5 mol % DMG-PEG2000 were superior in eliciting an antigen specific immune response compared to SLP (FIG. 3).

Materials and Methods for Examples 4-8

Animals

All mice experiments were performed with approval from the Utrecht Animal Welfare Body of the UMC Utrecht or by the Animal Ethics Committee of Ghent University. Animal care was according to established guidelines. All mice had unlimited access to water and standard laboratory animal chow. Female C57Bl/6J mice were obtained from Charles River Laboratories, Inc. (Germany/France).

mRNA Synthesis and Purification

Codon optimized E7, TriMix and luciferase mRNAs were prepared by eTheRNA by in vitro transcription (IVT) from eTheRNA plasmids. No nucleotide modifications were used. The E7 mRNA used in the DOE was ARCA capped. All later experiments were performed using CleanCapped mRNAs. After IVT, dsRNA was removed by cellulose purification. mRNA quality was monitored by capillary gel electrophoresis (Agilent, Belgium). Cleancap® Cy5-labelled Fluc mRNA (5-methoxyuridine modified and silica purified) was purchased from TriLink Biotechnologies.

LNP Production and Characterization

For biodistribution and cellular uptake studies, LNPs were loaded with a mixture of Firefly luciferase (Fluc) encoding mRNA (eTheRNA immunotherapies NV) and Cleancap® Cy5-labelled Fluc mRNA (TriLink Biotechnologies) in a 1:1 ratio. For the DoE immunogenicity study, LNPs were loaded with E7 mRNA. All other studies were performed with a mixture of E7, mouse CD40L, mouse CD70 and constitutively active TLR4 mRNA in a 3:1:1:1 ratio. The mRNA was diluted in 100 mM sodium acetate buffer (pH 4) and lipids were dissolved and diluted in ethanol. The mRNA and lipid solutions were mixed using a NanoAssemblr Benchtop microfluidic mixing system (Precision Nanosystems) followed by dialysis overnight against Tris-buffered saline (TBS, 20 mM Tris, 0.9% NaCl, pH 7.4). Amicon Ultra Centrifugal Filters (10 kD) were used for concentration of LNPs. Size, polydispersity index and zeta potential was measured with a Zetasizer Nano (Malvern). mRNA encapsulation efficiency was determined via ribogreen assay (ThermoFisher). Composition of all LNPs are summarized in table 2.

T Cell Response

Mice were immunized intravenously via the tail vein with 10 μg of mRNA in selected LNPs in a weekly interval. Blood for flow cytometry stainings was collected 5 to 7 days after immunizations. After lysing of red blood cells, the cells were incubated with FcR block and viability dye. After incubation and washing, APC labelled $E7_{(RAHYNIVTF)}$-tetramer was added and incubated at RT for 30 minutes. Excess tetramer was washed away and an antibody mixture for surface molecules CD3 and CD8 was added to the cells and incubated for 30 minutes at 4° C. Samples were acquired on a 3-laser AtuneNxt flow cytometer or a 4-laser BD LSR-Fortessa flow cytometer.

Intracellular cytokine production was determined in spleen 7 days after the third immunization. Single cell suspensions of splenocytes were prepared by crushing the spleens, lysing the red blood cells and filtering the samples over a 40 μM cell strainer. 200.000 cells/well/sample were plated in duplicate in a 96 well plate. 4 ug of E7 peptide (Genscript) was added for stimulation before cells were incubated at 37° C. After 1 hour of peptide stimulation, GolgiPlug (BD Cytofix/Cytoperm kit (BD Biosciences)) was added. Cells were incubated for another 4 hours. Hereafter, cells were incubated with FcR block and viability dye. After incubation and washing, APC labelled $E7_{(RAHYNIVTF)}$-textramer was added and incubated at RT for 30 minutes. Excess dextramer was washed away and an antibody mixture for surface molecules CD3 and CD8 was added to the cells and incubated for 30 minutes at 4° C. Further steps were according to the manufacturer's instructions of the BD Cytofix/Cytoperm kit (BD Biosciences). After permeabilization, cells were stained for IFN-γ and TNF-α. Samples were acquired on a 4-laser BD LSR-Fortessa flow cytometer. Analysis was done using FlowJo software.

Inflammatory Cytokines

Blood samples were collected in tubes with gel clotting factor (Sarstedt) 6 hours after each immunization (day 0, 7, 14 and 50). Clotted blood samples were centrifuged for 5 min at 10.000 g to obtain serum. Serum samples were stored at −80° C. until analysis. ProcartaPlex multiplex assay (ThermoFisher) was used to determine concentration of IFN-α, IFN-γ, IP-10. Serum samples were diluted 3 times in assay buffer and incubated with fluorescently labelled beads for 120 minutes. Further steps were performed according to protocol. Samples were acquired on a MagPix instrument (Luminex). Data was analysed using ProcartaPlex Analyst software.

TC-1 Tumor Experiment

TC-1 cells were obtained from Leiden University Medical Center. 0.5 million TC-1 cells in 50 μL PBS were injected subcutaneously on the right flank of the mice. Tumor measurements were performed using a caliper. Tumor volume was calculated as (smallest diameter$^2$×largest diameter)/2. Ant-PD-1 and isotype control antibodies were freshly diluted in PBS to a concentration of 200 μg in 200 μL per mouse and injected intraperitoneally. Mice received either antiPD-1 antibody (monotherapy or combined with mRNA LNP immunization) or isotype control (combined with LNP immunization). Antibodies were injected every 3 to 4 days starting 3 days after the first mRNA LNP immunization and ending 2 weeks after the last LNP injection. For analysis of tumor infiltrating lymphocytes, tumors were isolated 3 days after the second mRNA LNP immunization and placed in a 24-well plate filled with MACS tissue storage buffer (Miltenyi Biotec). Tumors were minced and incubated in digestion buffer for 1 hour with regular shaking. Hereafter, red blood cells were lysed and all samples were filtered over a 70 μM cell strainer. Lymphocytes were enriched by ficoll-Paque density gradient purification before proceeding with staining. First, the cells were incubated with FcR block and viability dye. After incubation and washing, APC labelled $E7_{(RAHYNIVTF)}$-tetramer was added and incubated at RT for 30 minutes. Excess tetramer was washed away and an antibody mixture for surface molecules CD45 and CD8 was added to the cells and incubated for 30 minutes at 4° C. Samples were acquired on a 3-laser AtuneNxt flow cytometer or a 4-laser BD LSRFortessa flow cytometer. Analysis was done using FlowJo software.

Biodistribution and Cellular Uptake

Mice were injected intravenously via the tail vein with 10 μg of mRNA in selected LNP formulations. After 4 hours, mice were anesthetized with 250 μL of pentobarbital (6 mg/mL). Blood samples were collected in tubes with gel clotting factor (Sarstedt). Subsequently, the chest cavity was opened, the portal vein was cut, and mice were perfused with 7 mL of PBS through the right ventricle. Organs were removed and snap-frozen in liquid nitrogen. For liver and spleen tissues, a part of the organ was kept in ice-cold PBS for flow cytometry analysis.

Cellular Uptake

Liver and spleen tissues were placed in petri dishes with RPMI 1640 medium containing 1 mg/mL Collagenase A (Roche) or 20 μg/mL Liberase™ (Roche), respectively, and 10 μg/mL DNAse I, grade II (Roche). Tissues were minced using surgical blades and incubated for 30 min at 37° C. Subsequently, tissue suspensions were passed through 100 μm nylon cell strainers. Liver suspensions were centrifuged for 3 min at 70×g to remove parenchymal cells. Supernatants and spleen suspensions were centrifuged 7 min at 500×g to pellet cells. Red blood cells were lysed in ACK buffer (Gibco) for 5 min, inactivated with PBS, and subsequently passed through a 100 μm cell strainer. Cells were washed with RPMI 1640 containing 1% fetal bovine serum (FBS), mixed with trypan blue and counted using a Luna-II Automated Cell Counter (Logos Biosystems). $3\times10^5$ (liver) or $6\times10^5$ (spleen) live cells were seeded in 96-well plates, pelleted for 5 min at 500×g and resuspended in 2% BSA in PBS (2% PBSA) containing 50% Brilliant Stain Buffer (BD Biosciences) and 2 μg/mL TruStain FcX (BioLegend). Cells were incubated for 10 min on ice and mixed 1:1 with 2% PBSA containing applicable antibody cocktails (three in total) in duplicate. Cells were incubated for 15 min at room temperature on a shaker, washed two times with 2% PBSA and were resuspended in 2% PBSA containing 0.25 μg/mL 7-AAD Viability Stain (BioLegend). Samples were acquired on a 4-laser BD LSRFortessa flow cytometer. Analysis was sone using FlowJo software.

Whole Body Distribution

Approximately 50-100 mg of each tissue was dissected, weighed and placed in 2 mL microtubes with a layer of approximately 5 mm of 1.4 mm ceramic beads (Qiagen). For each mg of tissue, 3 μL of cold Cell Culture Lysis Reagent (Promega) was added, and tissues were homogenized using a Mini-BeadBeater-8 (BioSpec) at full speed for 60 s at 4° C. Homogenates were stored at −80° C., thawed, centrifuged at 10.000×g for 10 min at 4° C. to remove beads and debris, and supernatants were stored again at −80° C. Ten microliters of each lysate was aliquoted in duplicate a white 96-well plate. Using a SpectraMax iD3 platereader equipped with injector, 50 μL of Luciferase Assay Reagent (Promega) was dispensed in each well while mixing, followed by a delay of 2 seconds and luciferase emission recording for 10 s. Luciferase activity was normalized for background signal obtained from organ lysates of mice injected with TBS.

Immune Cell Activation

Mice were injected intravenously via the tail vein with 5 μg of mRNA in selected LNPs. Spleens were harvested 4 hours later for flow cytometry staining. Single cell suspensions of splenocytes were prepared and incubated with digestion buffer (DMEM with DNAse-1 and collagenase-III) for 20 minutes with regular shaking. Hereafter, samples were incubated with Fc block and viability dye. After incubation and washing, cells were stained with cell lineage markers and activation markers. Samples were acquired on a 3-laser AtuneNxt flow cytometer. Analysis was done using FlowJo software.

Example 4—DOE Driven-Optimization of LNP Composition for Maximal T Cell Response LNP-libraries were created by combining the commercially available ionizable lipid Coatsome SS-EC with cholesterol, DOPE and a PEGylated lipid. DOPE is already part of several approved liposomal products and mRNA-vaccines under investigation. For the current experiment, different LNP compositions comprising DMG-PEG2000 were explored.

A first LNP-library was designed to address whether lipid molar ratios impact the T-cell response elicited by i.v. mRNA-LNP-vaccination and hence represent a variable that can be optimized to improve vaccine potency. The molar percentages of SS-EC, DOPE and PEG-lipid were considered as independent variables, whereas cholesterol was considered a filler lipid to balance the molar percentage to 100%. By using DOE-methodology, an experimental design involving 11 LNPs was created (see composition in table 3).

TABLE 2 composition of DMG-PEG2000 LNPs in the DOE experiment

| LNP number | Lipid ratio CoatsomeSS-EC/DOPE/Cholesterol/DMG-PEG2000 |
|---|---|
| LNP1 | 50/15/33.75/1.25 |
| LNP2 | 50/5/43.75/1.25 |
| LNP3 | 40.5/12.24/46.48/0.78 |
| LNP4 | 59.5/12.24/46.48/0.78 |
| LNP5 | 40.5/12.24/45.54/1.72 |
| LNP6 | 59.5/12.24/26.54/1.72 |
| LNP7 | 36.6/7.76/54.39/1.25 |
| LNP8 | 63.4/7.76/27.59/1.25 |
| LNP9 | 50/7.76/41.66/0.58 |
| LNP10 | 50/7.76/40.32/1.92 |
| LNP11 | 50/10/38.75/1.25 |

Figure 4:
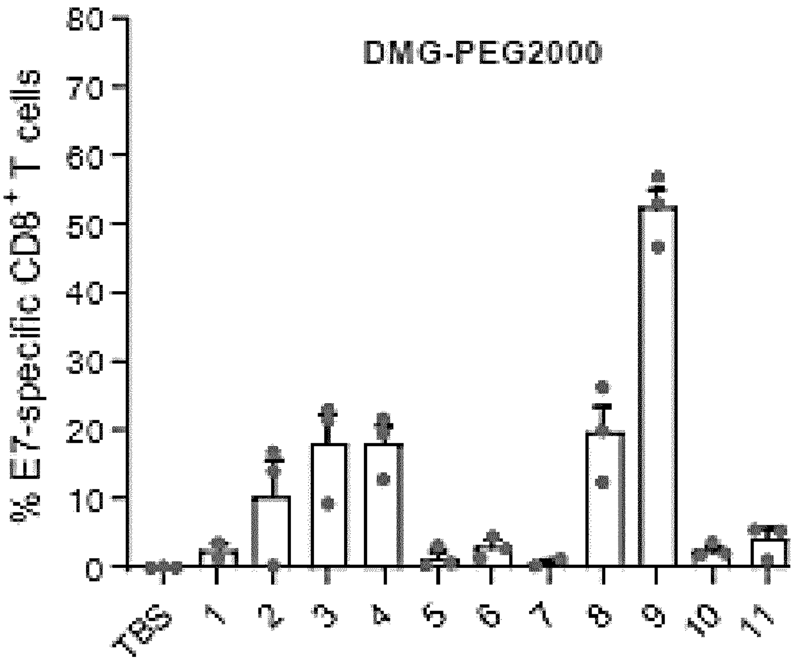
FIG. 4: DOE-driven optimization of LNP composition for maximal T cell responses. A, E7-specific T cells in blood after three immunizations (weekly interval) with E7 mRNA LNPs of DOE library. B. E7-specific CD8 T cell response in function of the % DMG-PEG2000 for the 11 LNPs of the DOE library.C, E7-specific T cells in blood after three immunizations (weekly interval) with predicted optimal LNP34 and non-optimal LNP35, Mean±SD is shown. Statistics were assessed by One-Way ANOVA with Sidak's multiple comparison test. ***p<0.001
Figure 4:
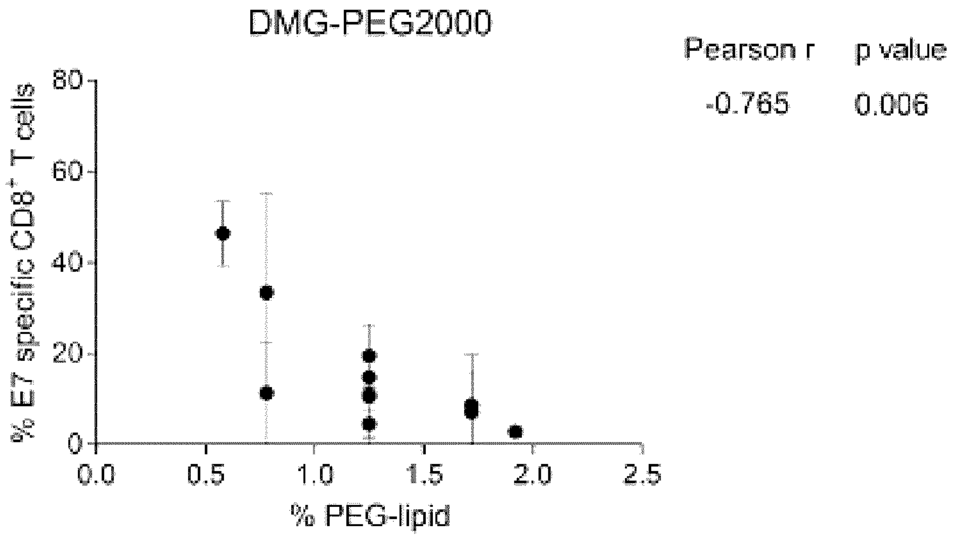
Figure 4C:
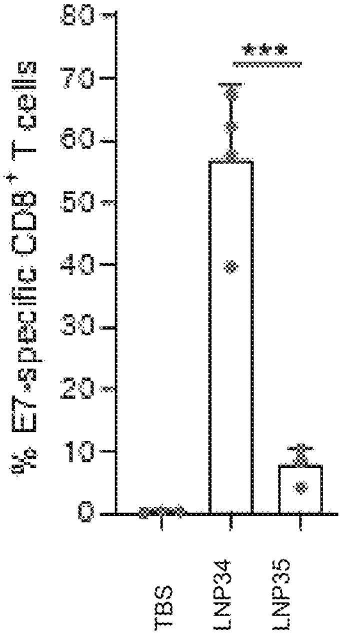

The 11 lipid ratios were uniformly distributed in the experimental domain (data not shown). For immunogenicity screening, the percentage of E7-specific CD8 T cells in blood after three i.v. immunizations was considered the response variable to be maximized. To this end, all LNPs packaged mRNA encoding the Human Papillomavirus 16 (HPV16) oncoprotein E7 as an antigen. Results confirm our assumption that the magnitude of the CD8 T-cell response is strongly dependent on the LNP-composition. Several mRNA-LNP-vaccines gave rise to over 50% of E7-specific CD8 T cell responses, whereas other mRNA-LNP-vaccines induced hardly any response (FIG. 4*a*). The molar % of DMG-PEG2000 was identified as a critical parameter in relation to the magnitude of the E7-specific CD8 T-cell response. Low molar percentages of PEG-lipid were required to achieve a maximum T-cell response (FIG. 4*c*).

Bayesian regression modelling was applied to the data to create response surface models (data not shown) that can predict the immunogenicity of a certain LNP-composition. To validate the predictive value of the models, 2 new LNP-compositions (table 3) were assessed.

TABLE 3 composition of DMG-PEG2000 LNPs in the DOE experiment

| LNP number | Lipid ratio CoatsomeSS-EC/DOPE/Cholesterol/DMG-PEG2000 |
|---|---|
| LNP34 | 56.5/5.25/37.75/0.5 |
| LNP35 (comparative example) | 42/12/44.5/1.5 |

Mice immunized with LNP34 (DMG-PEG2000) had an over 90% probability to elicit >30% E7-specific CD8 T cells (optimal LNPs), whereas LNP35 (DMG-PEG2000), was predicted to yield poor T-cell responses (non-optimal LNPs). The experimental data largely matched the predictions and hence successfully validated the model. All mice immunized with the predicted optimal LNPs indeed mounted an E7-specific CD8 T-cell response above 30%, while none of the mice immunized with LNP35 elicited T-cell responses above this threshold (FIG. 4*b*).

Example 5—mRNA Vaccines Induce Qualitative T Cell Responses

The success of cancer immunotherapy is impacted by a multitude of factors, including the T cell phenotype, functionality and tumor infiltration. We first assessed the quality and boostability of the T-cell response evoked by LNP34. To this aim, mice received three prime immunizations at days 0, 7 and 14 followed by a final immunization at day 50. E7 mRNA was supplemented with TriMix, a mix of 3 immunostimulatory mRNAs (Bonehill et al., 2008), which increases the strength of the T-cell response.

Figure 5:
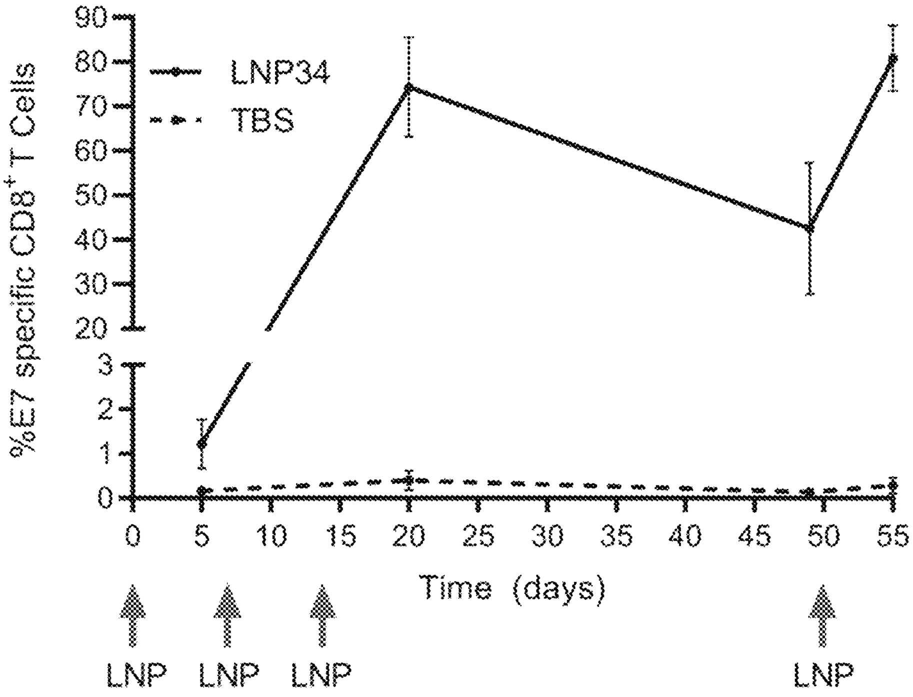
FIG. 5: Optimized mRNA LNP vaccines induce qualitative T cell responses and strong anti-tumor efficacy. A, Kinetics of E7-specific $CD8^+$ T cells in blood. B, IFN-γ in serum increases with repeated immunization C. Production of IFN-γ and TNF-α by splenic $CD8^+$ E7-specific T cells in spleen after three immunizations D Average TC-1 tumor growth in LNP34 immunized mice E, Survival of LNP34 immunized mice. F, TC-1 tumor infiltrating lymphocytes (TIL) after two immunizations with LNP34. G, E7-specificity of TILs. A, B, F, G, Mean±SD is shown. C, Mean±SEM is shown. D, Statistics were assessed by Mantel-Cox log rank rank test. F, G, Statistics were assessed by One-Way ANOVA with Tukey's multiple comparison test , p<0.01, *p<0.001, ns=not significant.
Figure 5:
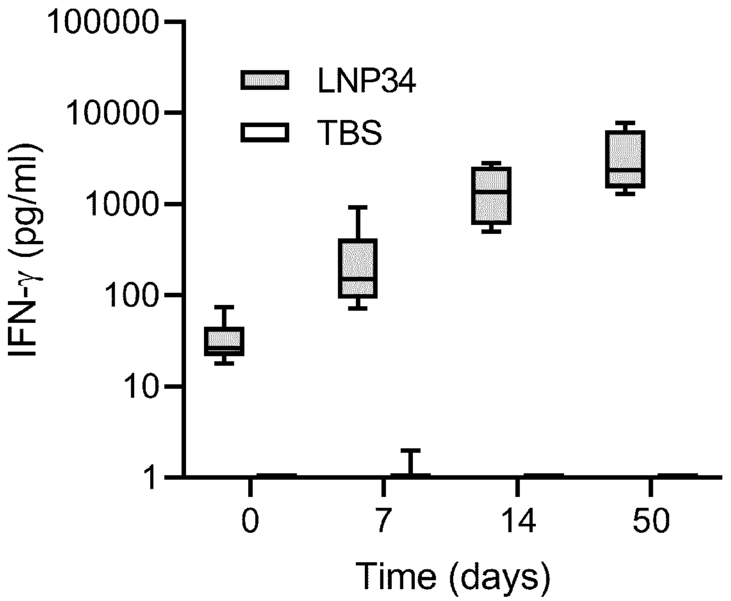
Figure 5:
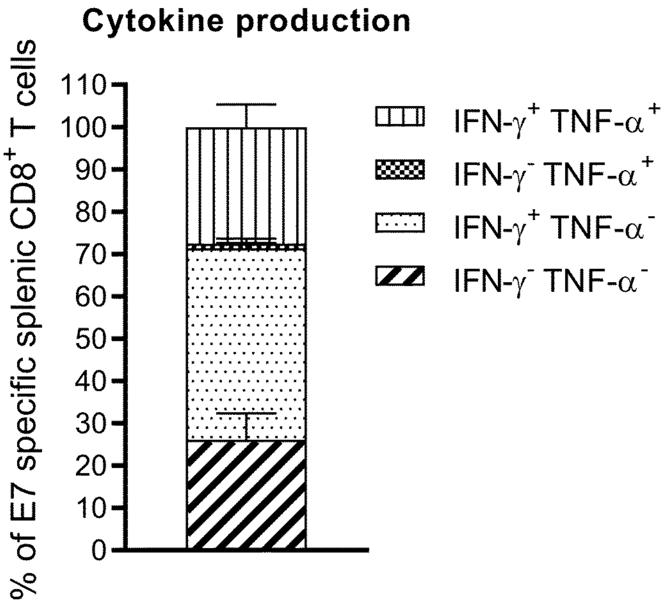
Figure 5:
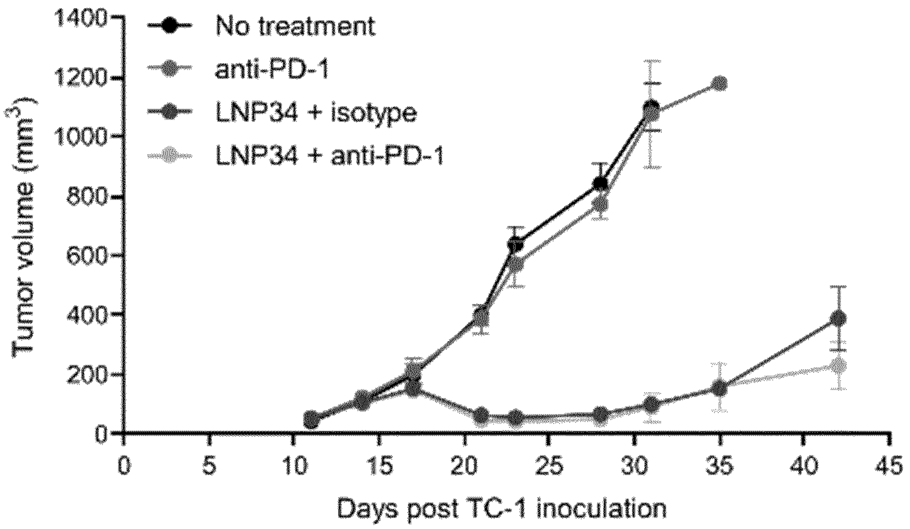
Figure 5:
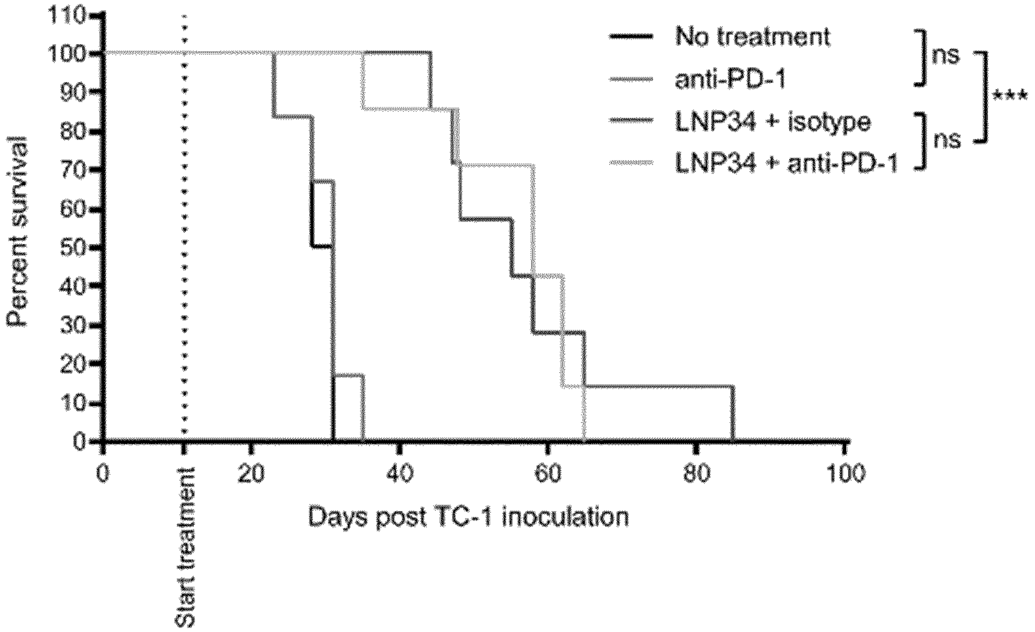
Figure 5:
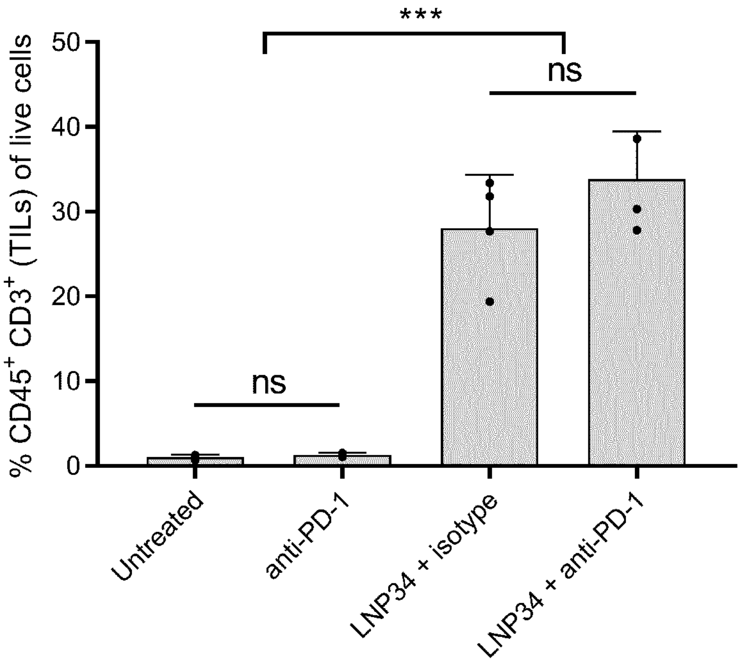
Figure 5:
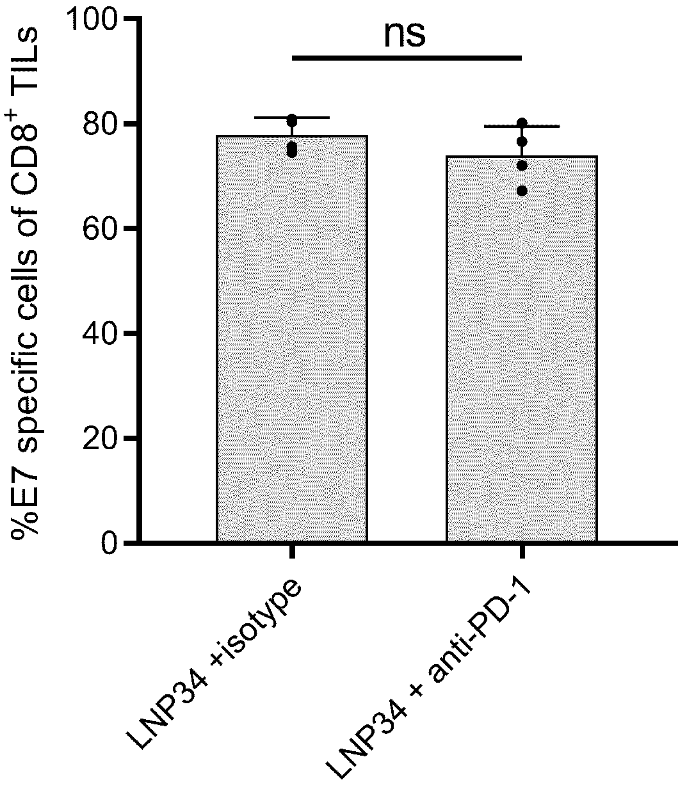

Following 3 immunizations with E7-TriMix, over 70% of E7-specific T cells were present in blood (FIG. 5*a*). Five weeks after the third immunization the percentage of E7-specific CD8 T cells had remained highly elevated. Upon administration of a final booster immunization a rapid expansion of E7-specific effector T cells was observed, hence demonstrating the vaccine is boostable (FIG. 5*a*). Higher concentrations of IFN-γ in serum was measured with every immunization (FIG. 5*b*), mirroring the increasing numbers of E7-specific T cells.

To assess T-cell functionality, we performed an intracellular cytokine staining after three immunizations. Polyfunctional CD8 T cells, who produce more than one cytokine simultaneously, are associated with better control of infectious diseases and tumors and accounted for approximately 28% of CD8 E7 specific T cells for the optimal LNPs (FIG. 5*c*).

Example 6—mRNA Vaccines Induce Tumor Regression

Therapeutic antitumor efficacy was assessed in syngeneic mouse tumor model TC-1, generated by retroviral transduction with HPV16 E6/E7 antigens. Treatment with 5 μg E7-TriMix delivered by LNP34 was initiated when tumors reached a mean diameter of 55 $mm^3$. In addition, mice were treated with anti-PD-1 (or isotype control antibody). PD-1 is expressed on activated T cells and upon interaction with PD-L1 inhibits T cell function and induces tolerance. PD-1 checkpoint blockade sustains T-cell reactivity and is approved for the first line treatment of patients with metastatic or unresectable recurrent HNSCC. LNP34 vaccination resulted in profound regression of TC-1 tumors (FIG. 5*d*) and significantly prolonged survival time (FIG. 5*e*), yet tumors relapsed after cessation of treatment. Anti-PD1 monotherapy did not provide any therapeutic benefit to TC-1 bearing mice.

Finally, we assessed the capacity of the vaccine elicited T cells to reach the tumorbed. Two vaccinations with the respective mRNA-LNP-vaccines led to a strong infiltration of $CD8^+$ tumor-infiltrating T cells into the tumor (FIG. 50, with over 70% being specific for E7 (FIG. 5*g*). Addition of anti-PD-1 to the vaccine treatment did not significantly alter the percentages of E7-specific CD8 T cells entering the tumor.

Figure 6:
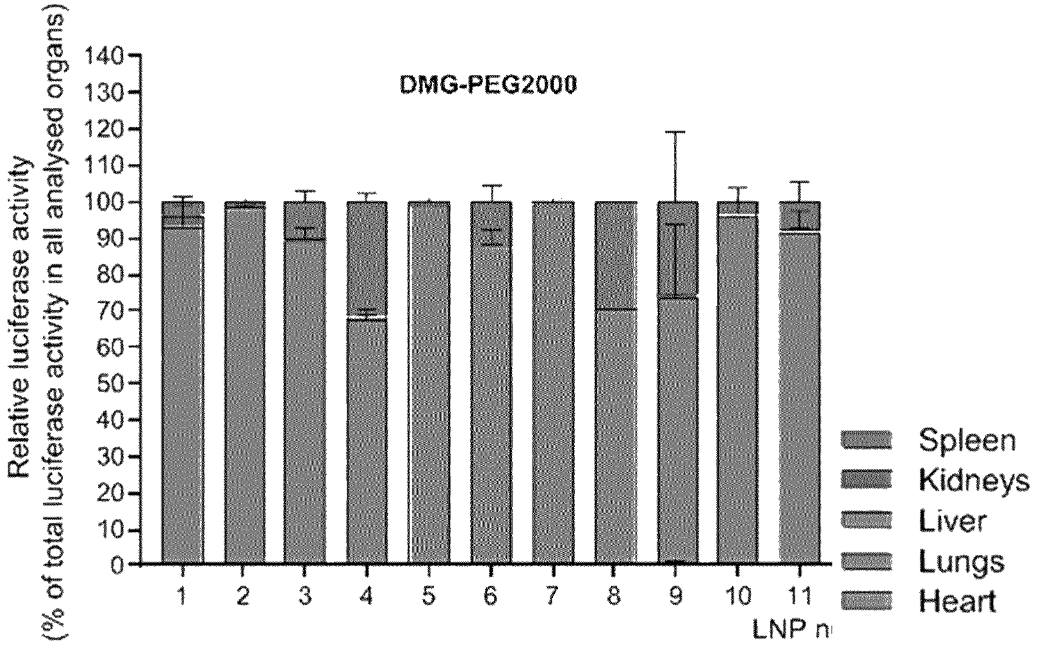
FIG. 6: LNPs are taken up by and activate a variety of (innate) immune cells.
Figure 6:
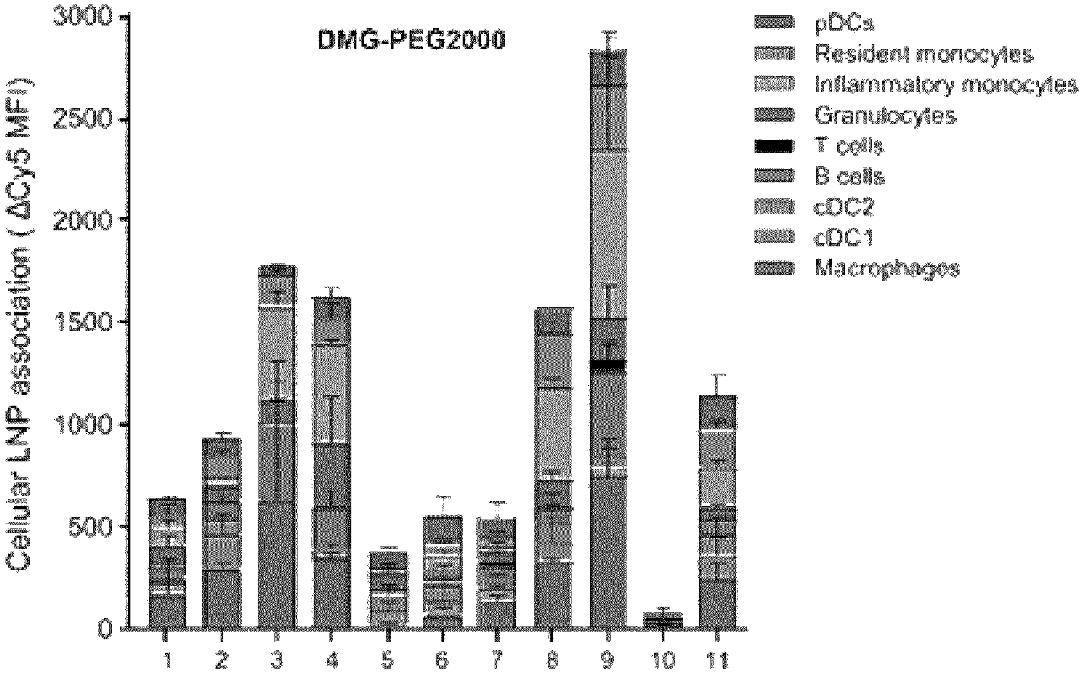
Figure 6:
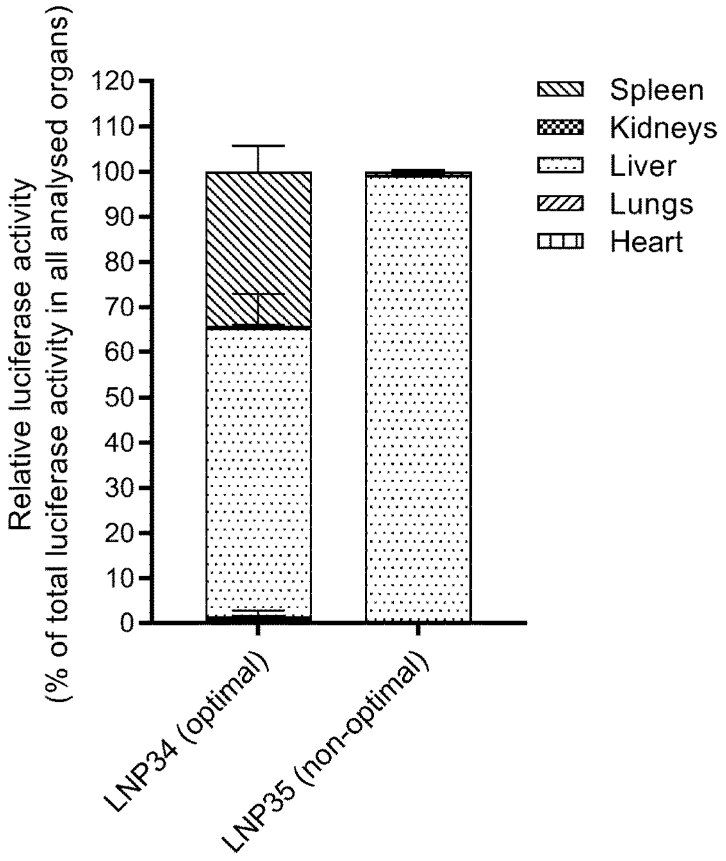
Figure 6:
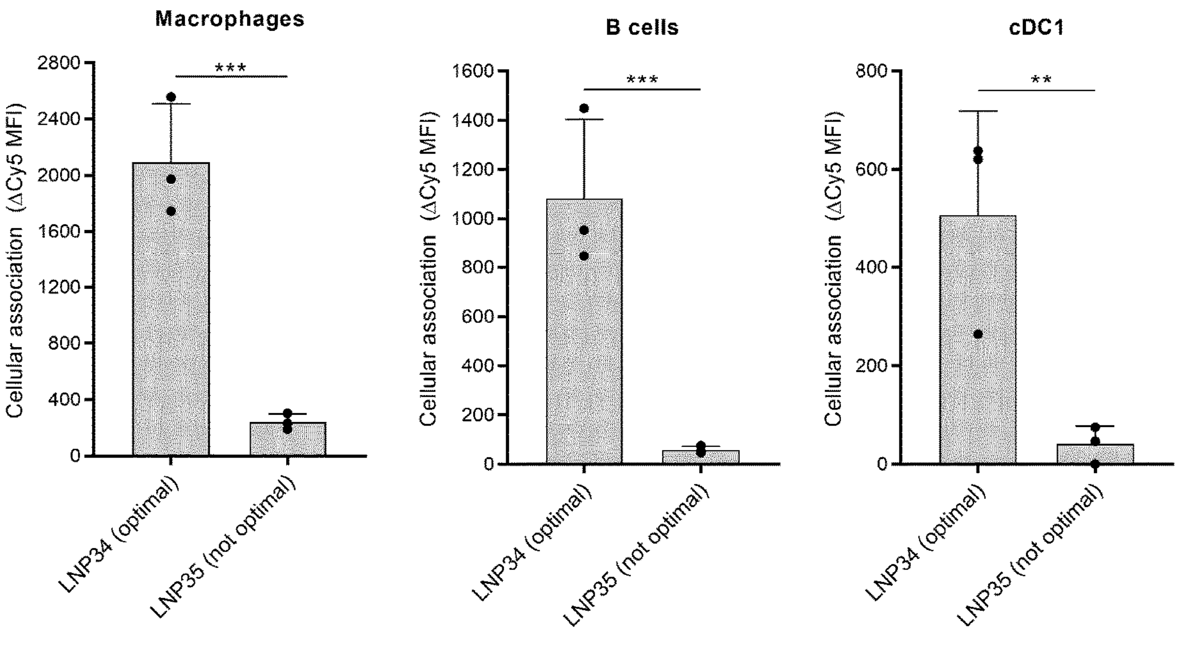
Figure 6F:
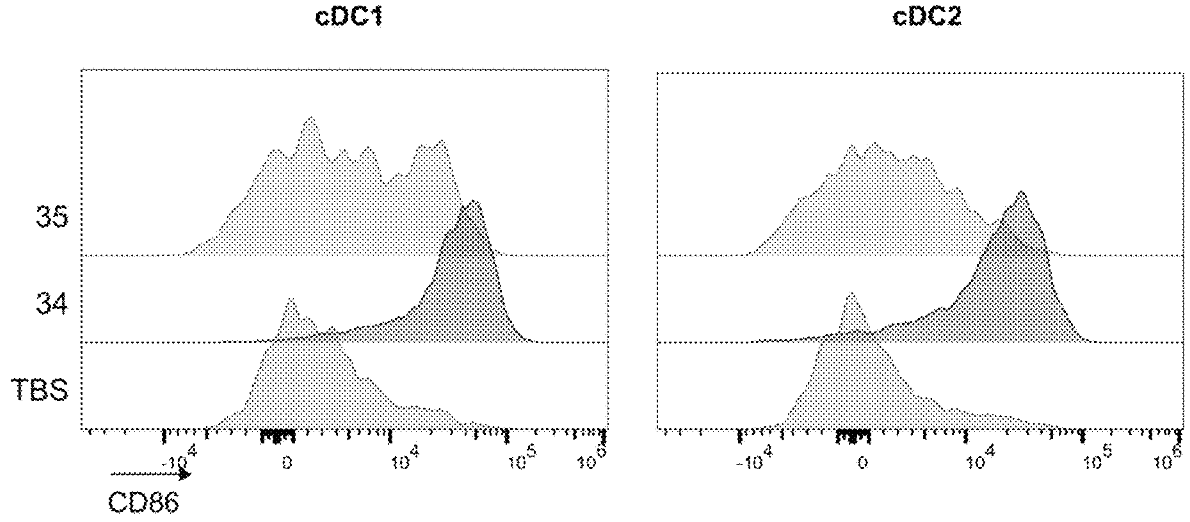
FIG. 6F. CD86 expression on cDC1 and cDC2 is weakly upregulated by non-optimal LNP35 and strongly upregulated by optimal LNP34 A-D. Mean±SD is shown. D, Statistics were assessed by One-Way ANOVA with Sidak's multiple comparison test. , p<0.01, *p<0.001, ns=not significant.

Example 7—Optimal LNPs Increase Uptake and Activate Immune Cells in the Spleen To address whether correlations exist between the magnitude of the evoked T-cell response and the biodistribution of mRNA uptake and expression at the organ and cell type level, we encapsulated Cy5-labeled Firefly Luciferase mRNA in the DMG-PEG2000 LNPs that were previously screened for immunogenicity. Luciferase activity was measured in isolated liver, spleen, lungs, heart and kidneys four hours after LNP-injection. As anticipated, LNP-composition had strong impact on the intensity and organ specificity of mRNA-expression. Liver was the primary target organ, followed by the spleen, but the ratio liver to spleen differed strongly between LNPs (FIG. 6*a*). The magnitude of the E7-specific CD8 T-cell response after the third immunization positively correlated with spleen expression. The importance of delivery to the spleen was further highlighted by the absence of correlation between total expression and T-cell responses (data not shown). Significant correlations were also identified between LNP size (strongly tangled with lipid composition).

We next assessed whether immunogenicity is linked to early mRNA-uptake and activation of specific immune cell types in the spleen. LNPs accumulated mainly in macrophages and monocytes (FIG. 6*b*). Strong overall correlations were existing between the T-cell response and LNP uptake by splenic macrophages, monocytes, plasmacytoid DCs (pDC) and B cells (data not shown).

To further validate the importance of mRNA-uptake and expression in the spleen we compared the biodistribution and cellular uptake profiles of the optimal, highly immunogenic LNP34 with the non-optimal, poorly immunogenic LNP35. Relative to LNP35, LNP34 dramatically increased relative mRNA-expression in the spleen (FIG. 6*c*) and uptake by macrophages, B cells and DCs in the spleen (FIG. 6*d*).

Compared to their suboptimal counterparts, the optimal mRNA LNP compositions LNP34 triggered higher levels of inflammatory cytokines in blood, indicative of increased innate activation (FIG. 6*e*).

Example 8—Further DMG-PEG2000 LNPs of the Invention

Figure 7:
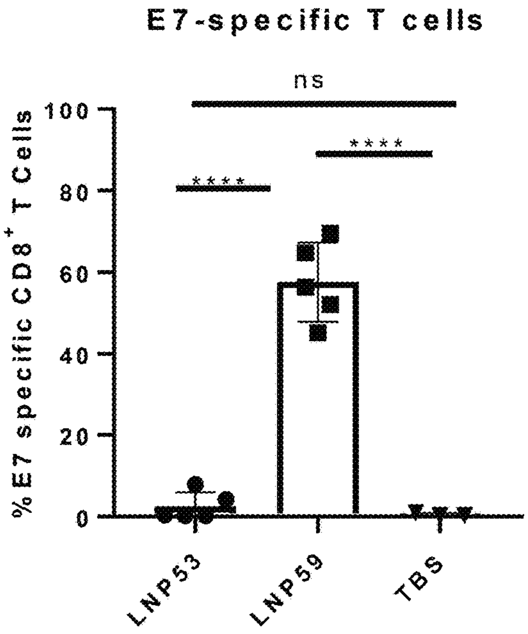
FIG. 7: E7-specific T cells in blood after two immunizations (weekly interval) with alternative optimal (LNP59) and non-optimal (LNP53) DMG-PEG2000 LNPs, Mean±SD is shown. Statistics were assessed by One-Way ANOVA with Sidak's multiple comparison test. ***p<0.001.

In this example further interesting LNPs were tested (see table 4). Mice were given 2 intravenous immunizations, 1 week apart from each other. E7-specific T cells in blood were analyzed 5 days after the second immunization. Data shown in FIG. 7 evidence that LNP59 performs significantly better than LNP53; and is accordingly also highly suitable in the context of the present invention. LNP59 is again characterized in having a low percentage of PEG lipid i.e. 0.5 mol %, but also has a significantly lower cholesterol level, i.e. less than 30 mol %; in particular about 25 mol %.

TABLE 4 composition of further DMG-PEG2000 LNPs

| LNP number | Lipid ratio CoatsomeSS-EC/DOPE/Cholesterol/DMG-PEG2000 |
|---|---|
| LNP53 (comparative example) | 50/10/38.5/1.5 |
| LNP59 | 65/9.5/25/0.5 |

CONCLUSIONS

LNP composition can be tuned for strong immunogenicity by modulation of lipid ratio's. Optimal LNP compositions showed increased expression in spleen, with enhanced uptake by multiple APC populations. Optimal LNPs induced high levels of type I IFN, which were found critica for the T cell response evoked. Surprisingly, most of the mRNA dose injected became associated with B cells. B cells showed an activated phenotype and were vital for induction of antigen-specific CD8 T cells, indicating a previously undocumented role of B cells.

The DoE approach successfully predicted LNP-compositions to be highly or poorly immunogenic. Optimal LNP-compositions promoted A) mRNA uptake and expression by splenic APCs, mainly B cells B) innate activation, evidenced by increased release of inflammatory cytokines and expression of activation markers on APCs C) high magnitude and qualitative T-cell responses, capable of regressing established TC-1 tumors. Induction of type I interferons was found critical in the efficacy of i.v. administrated mRNA-vaccines. Also B cells were crucial for the induction of T-cell responses, likely partially due to the production of anti-PEG antibodies. Importantly, the presence of antibodies against the LNPs does not interfere with eliciting T-cell responses. This is highly relevant considering that many people will acquire PEG-antibodies after vaccination with PEGylated LNPs.

The invention claimed is:

1. A lipid nanoparticle comprising:

an ionizable lipid;

a phospholipid;

a sterol;

a PEG lipid; and one or more mRNA molecules, wherein:

the PEG lipid is a C14-PEG lipid;

the lipid nanoparticle comprises from about 0.5 mol % to about 0.9 mol % of the PEG lipid;

the molar percentage of the ionizable lipid is from about 55 mol % to about 60 mol %;

the molar percentage of the phospholipid is from about 5 mol % to about 10 mol %; and the molar percentage of the sterol is from about 25 mol % to about 39.5 mol %.

2. The lipid nanoparticle of claim 1, wherein the molar percentage of the sterol is from about 30 mol % to about 39.5 mol %.

3. The lipid nanoparticle of claim 1, wherein the ratio of ionizable lipid to phospholipid is greater than 5:1.

4. The lipid nanoparticle of claim 1, wherein the ratio of ionizable lipid to phospholipid is from about 6:1 to about 11:1.

5. The lipid nanoparticle of claim 1, wherein the ratio of ionizable lipid to phospholipid is about 11:1.

6. The lipid nanoparticle of claim 1, wherein the C14-PEG lipid is a C14-PEG2000 lipid.

7. The lipid nanoparticle of claim 1, wherein the C14-PEG lipid is selected from DMG-PEG2000 or DMPE-PEG2000.

8. The lipid nanoparticle of claim 1, wherein the ionizable lipid is selected from:

1,1'-((2-(4-(2-((2-(bis(2-hydroxydodecyl)amino)ethyl)(2-hydroxydodecyl)amino)ethyl) piperazin-1-yl)ethyl) azanediyl)bis(dodecan-2-ol) (C12-200);

dilinoleylmethyl-4-dimethylaminobutyrate (DLin-MC3-DMA); or a compound of formula (I):

(I)

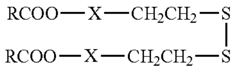

wherein:

RCOO is selected from myristoyl, α-D-tocopherolsuccinoyl, linoleoyl, or oleoyl; and X is selected from:

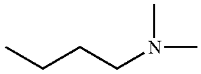
and
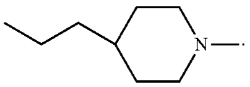

9. The lipid nanoparticle of claim 1, wherein the ionizable lipid is a compound of formula (I), where RCOO is α-D-tocopherolsuccinoyl and X is

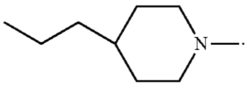

10. The lipid nanoparticle of claim 1, wherein the phospholipid is selected from DOPE, DOPC, DSPC, or mixtures thereof.

11. The lipid nanoparticle of claim 1, wherein the phospholipid is selected from DOPE, DOPC, or mixtures thereof.

12. The lipid nanoparticle of claim 1, wherein the sterol is selected from cholesterol, ergosterol, campesterol, oxysterol, antrosterol, desmosterol, nicasterol, sitosterol, or stigmasterol.

13. The lipid nanoparticle of claim 1, wherein the sterol is cholesterol.

14. The lipid nanoparticle of claim 1, comprising:

about 56.5 mol % of the ionizable lipid;

about 5 mol % DOPE;

about 38 mol % cholesterol; and about 0.5 mol % DMG-PEG2000.

15. A lipid nanoparticle, comprising:

about 65 mol % of the ionizable lipid;

about 9.5 mol % DOPE;

about 25 mol % cholesterol;

about 0.5 mol % DMG-PEG2000; and one or more mRNA molecules.

16. The lipid nanoparticle of claim 1, wherein the one or more mRNA molecules are selected from immunomodulatory polypeptide-encoding mRNA or antigen-encoding mRNA.

17. A lipid nanoparticle of claim 1, wherein the one or more mRNA molecules comprise mRNA molecules encoding for CD40L, mRNA molecules encoding for CD70, and mRNA molecules encoding for caTLR4.

18. A pharmaceutical composition or a vaccine comprising one or more lipid nanoparticles according to claim 1 and an acceptable pharmaceutical carrier.

* * * * *